US009492556B2

(12) United States Patent
Jain et al.

(10) Patent No.: US 9,492,556 B2
(45) Date of Patent: *Nov. 15, 2016

(54) N-TERMINAL DERIVATISATION OF PROTEINS WITH POLYSACCHARIDES

(71) Applicant: Lipoxen Technologies Limited, London (GB)

(72) Inventors: Sanjay Jain, London (GB); Peter Laing, London (GB); Gregory Gregoriadis, London (GB)

(73) Assignee: Lipoxen Technologies Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/614,406

(22) Filed: Feb. 4, 2015

(65) Prior Publication Data
US 2015/0147307 A1 May 28, 2015

Related U.S. Application Data

(63) Continuation of application No. 13/794,692, filed on Mar. 11, 2013, now Pat. No. 8,981,050, which is a continuation of application No. 12/375,012, filed as application No. PCT/GB2007/002839 on Jul. 25, 2007, now Pat. No. 8,394,921.

(30) Foreign Application Priority Data

Jul. 25, 2006 (EP) .................................... 06117830

(51) Int. Cl.
| *A61K 38/00* | (2006.01) |
| *A61K 47/48* | (2006.01) |
| *A61K 38/18* | (2006.01) |
| *C07K 14/535* | (2006.01) |
| *C07K 14/52* | (2006.01) |
| *C07K 14/505* | (2006.01) |
| *C07K 14/575* | (2006.01) |
| *A61K 38/46* | (2006.01) |
| *A61K 38/19* | (2006.01) |

(52) U.S. Cl.
CPC ........ *A61K 47/4823* (2013.01); *A61K 38/1816* (2013.01); *A61K 38/193* (2013.01); *A61K 38/465* (2013.01); *C07K 14/505* (2013.01); *C07K 14/52* (2013.01); *C07K 14/535* (2013.01); *C07K 14/575* (2013.01); *A61K 38/00* (2013.01); *C12Y 301/21001* (2013.01)

(58) Field of Classification Search
None
See application file for complete search history.

(56) References Cited

U.S. PATENT DOCUMENTS

| 6,323,311 B1 | 11/2001 | Liu et al. | |
| 6,329,347 B1* | 12/2001 | Phillips ................. | A61K 31/711 424/93.2 |
| 6,956,027 B2 | 10/2005 | Kinstler | |
| 6,962,972 B2 | 11/2005 | Gregoriadis | |
| 7,074,755 B2 | 7/2006 | Heavner | |
| 7,128,913 B2 | 10/2006 | Burg et al. | |
| 7,691,635 B2* | 4/2010 | Laayoun ............... | C07D 495/04 435/6.15 |
| 7,807,824 B2 | 10/2010 | Jain et al. | |
| 7,875,708 B2 | 1/2011 | Jain et al. | |
| 8,394,921 B2* | 3/2013 | Jain .................... | A61K 47/4823 530/322 |
| 8,475,765 B2* | 7/2013 | Zander ................ | A61K 9/0021 424/1.41 |
| 8,981,050 B2* | 3/2015 | Jain .................... | A61K 47/4823 530/322 |
| 2004/0043446 A1* | 3/2004 | DeFrees ................ | C07K 1/006 435/68.1 |
| 2004/0082765 A1 | 4/2004 | Nakamura et al. | |
| 2005/0143292 A1* | 6/2005 | DeFrees ............... | C07K 14/505 514/1.3 |
| 2006/0228347 A1* | 10/2006 | Sunaga ................ | A61K 9/1271 424/94.6 |
| 2007/0014759 A1 | 1/2007 | DeFrees et al. | |
| 2007/0083006 A1 | 4/2007 | Hinds et al. | |

FOREIGN PATENT DOCUMENTS

| CA | 1156217 | 11/1983 |
| EP | 0550108 A1 | 7/1993 |
| EP | 1 219 636 | 7/2003 |

(Continued)

OTHER PUBLICATIONS

Ganglioside GD1alpha analogues as high-affinity ligands for myelin-associated glycoprotein (MAG). Carbohydrate Research. 1999. vol. 316, pp. 1-5.*
First Examination Report issued on Mar. 26, 2014, in Indian National Phase 573/DELNP/2009.
Brownlee, M. et al., "A Glucose Controlled Insulin Delivery System Semi Synthetic Insulin Bound to Lectin" Science, (Washington DC), vol. 206, No. 4423, 1979, pp. 1190-1191.
Caliceti, P., (1999) "Improvement of the physiochemical and biopharmaceutical properties of insulin by poly (ethyleneglycol) conjugation." STP Pharma Sciences 9:107-113.
DeFrees, S. et al., "GlycoPEGylation of recombinant therapeutic proteins produced in *Escherichia coli.*", Glycobiology. Sep. 2006; 16(9): 833-43. Epub May 22, 2006.
Ehrat, M., Luisi P.L., 1983 "Synthesis and spectroscopic characterization of insulin derivatives containing one or two poly(ethylene oxide) chains at specific positions." Biopolymers, 22:569-73.
Fan, Q. et al., "Preclinical evaluation of Hematide, a novel erthryopoiesis stimulating agent, for the treatment of anemia." Exp. Hematol., Oct. 2006;34(10):1303-11.

(Continued)

*Primary Examiner* — Marcela M Cordero Garcia
(74) *Attorney, Agent, or Firm* — One3 IP Management, P.C.; Annette S. Parent; Dean G. Stathakis

(57) ABSTRACT

The present invention relates to methods for producing N-terminal derivatives of proteins in which a polysaccharide, preferably having at least terminal sialic units, and preferably consisting essentially only of sialic acid units, is reacted at the N-terminus of a protein or peptide under controlled conditions to produce an N-terminal derivative. The controlled conditions include use of acidic pH for the derivatization step and a higher pH for purification. The derivatives are useful for improving pharmacokinetics and pharmacodynamics of proteins and peptides.

19 Claims, 21 Drawing Sheets

(56) References Cited

FOREIGN PATENT DOCUMENTS

| | | |
|---|---|---|
| EP | 1681303 | 7/2006 |
| JP | 2003-533537 | 11/2003 |
| RU | 2 141 531 | 11/1999 |
| WO | WO 91/05867 | 5/1991 |
| WO | WO 92/22331 | 12/1992 |
| WO | WO 99/43307 A1 | 9/1999 |
| WO | WO 01/87272 A2 | 11/2001 |
| WO | WO 01/87922 A2 | 11/2001 |
| WO | WO 03/031464 | 4/2003 |
| WO | WO 03/055526 | 7/2003 |
| WO | WO 2004/091494 | 10/2004 |
| WO | WO 2004/101619 | 11/2004 |
| WO | WO 2005/003149 | 1/2005 |
| WO | WO 2005/014050 | 2/2005 |
| WO | WO 2005/016973 A1 | 2/2005 |
| WO | WO 2005-016974 A1 | 2/2005 |
| WO | WO 2005/037320 A2 | 4/2005 |
| WO | WO 2005/055946 | 6/2005 |
| WO | WO 2006/014148 | 2/2006 |
| WO | WO 2006-016161 A1 | 2/2006 |
| WO | WO 2006/016168 A2 | 2/2006 |
| WO | WO 2006/000540 | 5/2006 |
| WO | WO 2006/074467 | 7/2006 |
| WO | WO 2006/082184 | 8/2006 |
| WO | WO 2006/090119 A1 | 8/2006 |
| WO | WO 2007/047922 | 4/2007 |
| WO | WO 2008/012540 | 1/2008 |

OTHER PUBLICATIONS

Geiger. et al., in D. Branderburg and A. Wollmer (eds.) 1980, Insulin: Chemistry, Structure, and Function of Insulin and Related Hormones. Walter de Gruyter & Co., New York, p. 409-15.
Hinds, K., et al. (2000) "Synthesis and Characterization of Poly-(ethylene glycol)-Insulin Congjugates," Bioconjugate Chem., 11, 195-201.
Molineux, G., "The design and development of pegfilgrastim (PEG-rmetHuG-CSF, Neulasta)," Curr. Pharm. Des. 2004 (Mar. 12, 2004), 10(11):1235-44.
Uchio T., et al. (1999) "Site-specific insulin conjugates with enhanced stability and extended action profile." Advanced Drug Delivery Reviews, 35, p. 289-306.
Jain et al., "Polysialylated insulin: synthesis, characterization and biological activity in vivo." Biochimica et Biophysica Acta, 1622 (2003) 42-49.
Gregoriadis et al., "Imroving the therapeutic efficacy of peptides and proteins: A role for polysialic acid." Int'l J. of Pharmaceutics, Amsterdam NL. v. 300, No. 1-2, Aug. 26, 2005, pp. 125-130.
Almeida and Souto, Adv. Drug. Delivery Rev. (2007) 59; 478-490.
Shafer et al., Vaccine (2000) 18:1273-1281.
International Preliminary Report on Patentability and Written Opinion of the International Searching Authority for PCT/GB2007/002839, issued Jan. 27, 2009, 5 pages.
International Search Report for PCT/GB2007/002839, mailed Dec. 10, 2007, 6 pages.
International Preliminary Report on Patentability and Written Opinion of the International Searching Authority for PCT/GB2007/002839, issued Feb. 3, 2009, 8 pages.
Fernandes and Gregoriadis, Biochmica et Biophysica Acta (1996) 1293:92-96.
Fernandes and Gregoriadis, Biochmica et Biophysica Acta (1997) 1341:26-34.
Gregoriadis et al., FEBS Letters (1993) 315:271-276.
Jain et al., Drug Delivery Systems and Sciences (2004) 4(2):3-9.
Kinstler et al., Advanced Drug Delivery Reviews (2002) 54(4):477-485.
Krystal, Exp. Hematol. (1983) 11(7):649-660.
Lifely et al., Carbohydrate Research (1981) 94:193-203.
Park and Johnson, J. Biol. Chem. (1949) 181:149-151.
Sinicropi et al., Anal. Biochem. (1994) 222(2): 351-358.
Svennerholm, Biochemica et Biophysica Acta (1957) 24:604-611.
Wang, International Journal of Pharmaceutics (1999) 185:129-188.
Hinds, K.D., "Effects of PEG conjugation on insulin properties" Adv. Drug Deliv. Rev. Jun. 17, 2002; 54(4):505-30.
Sato et al., "Site-specific introduction of sialic acid into insulin." Angewandte Chemi. International Edition, Wiley VCH Verlag, Weinheim, DE, vol. 43, No. 12 Mar. 12, 2004, pp. 1516-1520.

\* cited by examiner

Figure 2.1
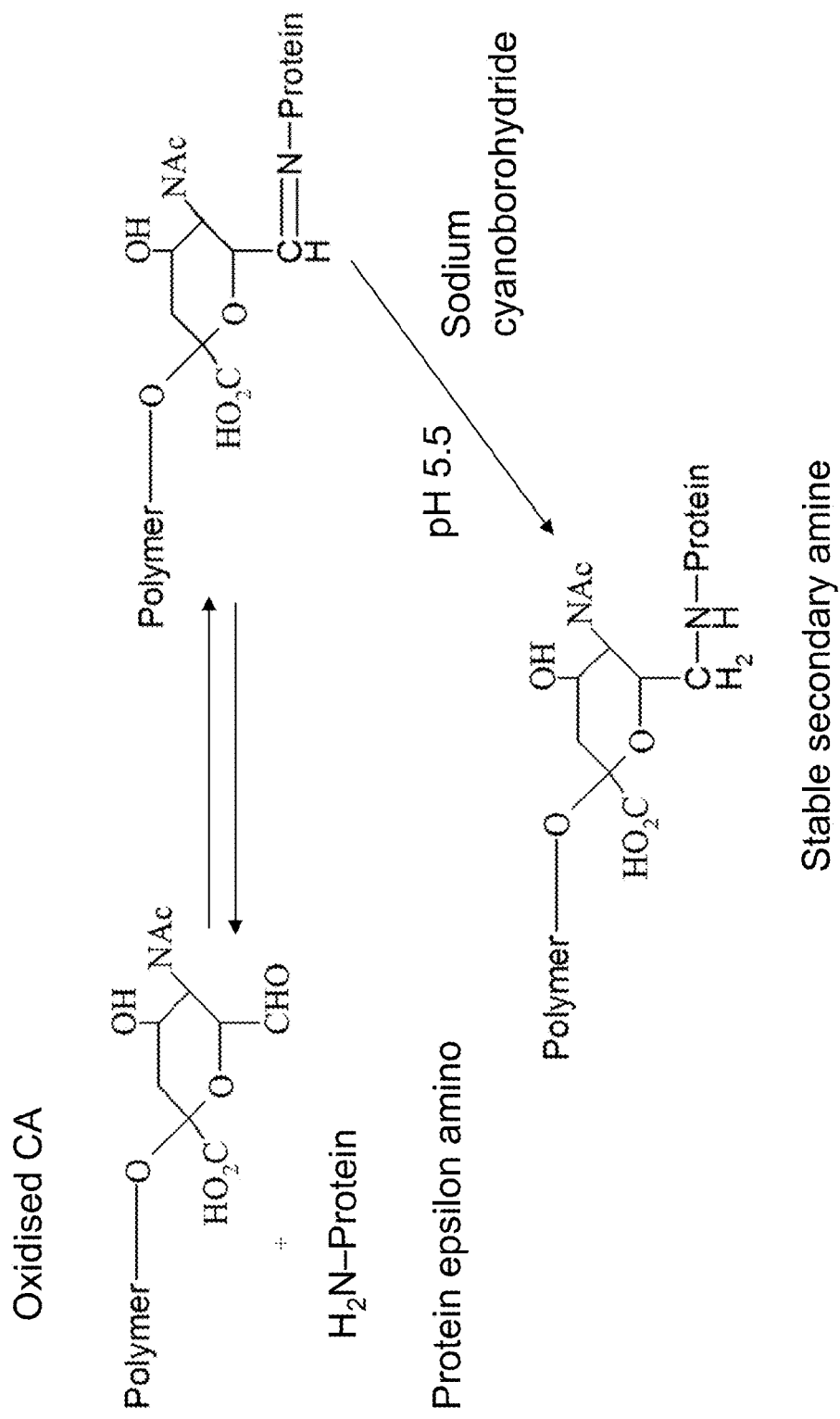

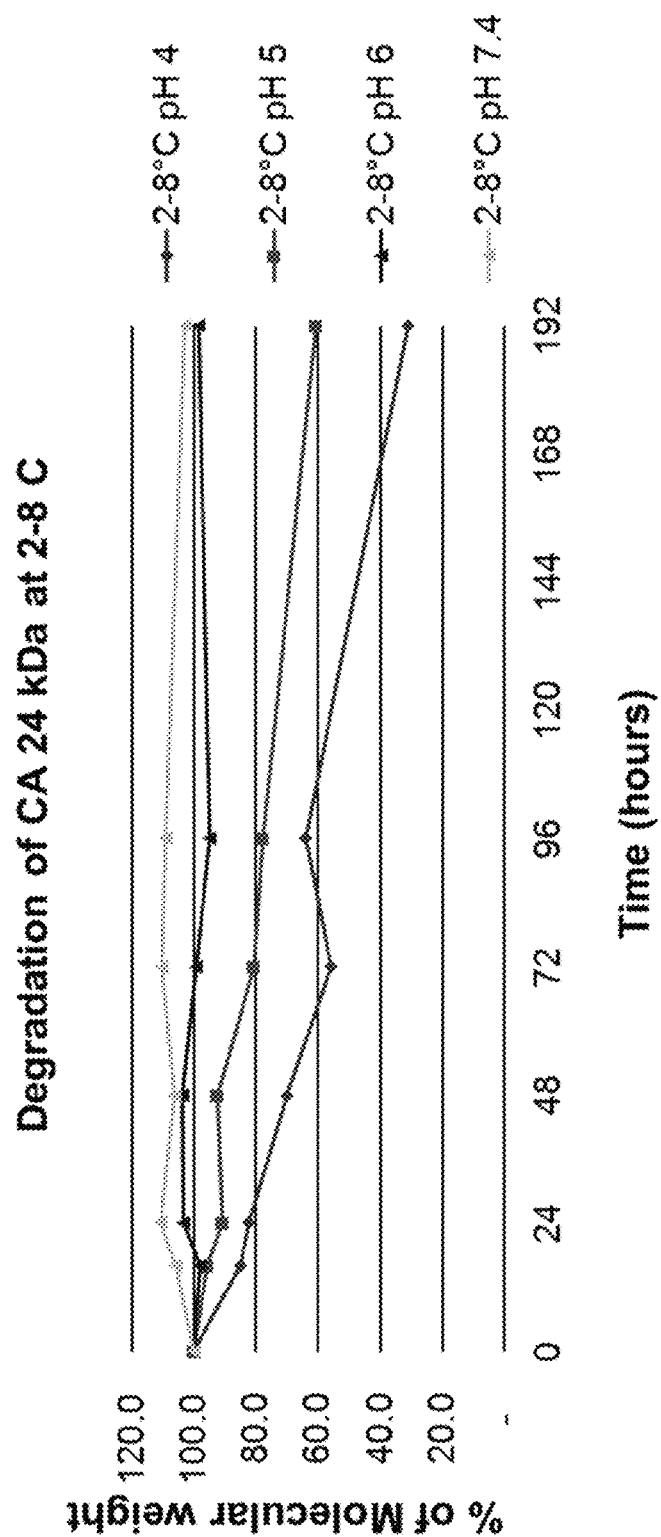
Figure 2.2

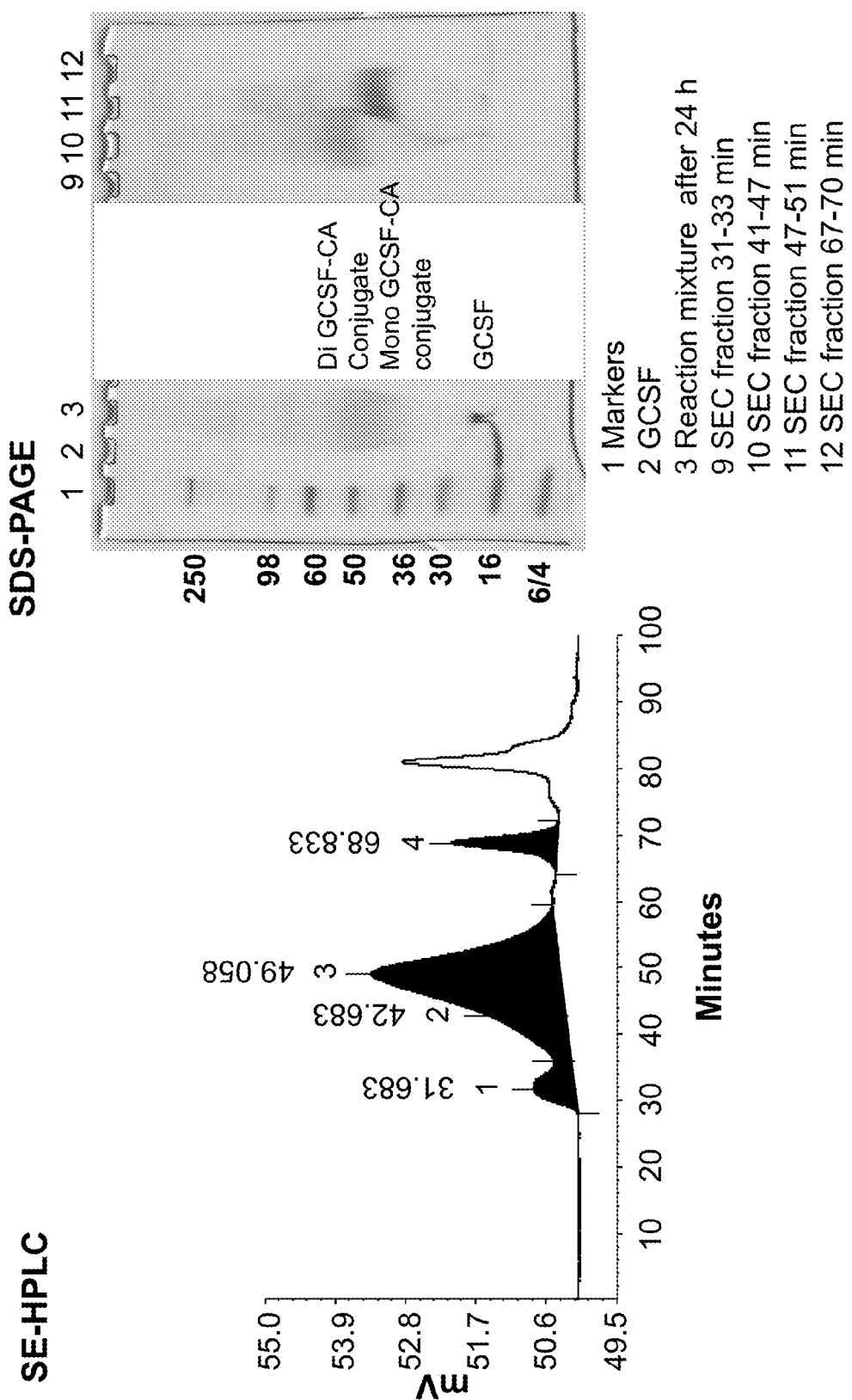
Figure 3.1

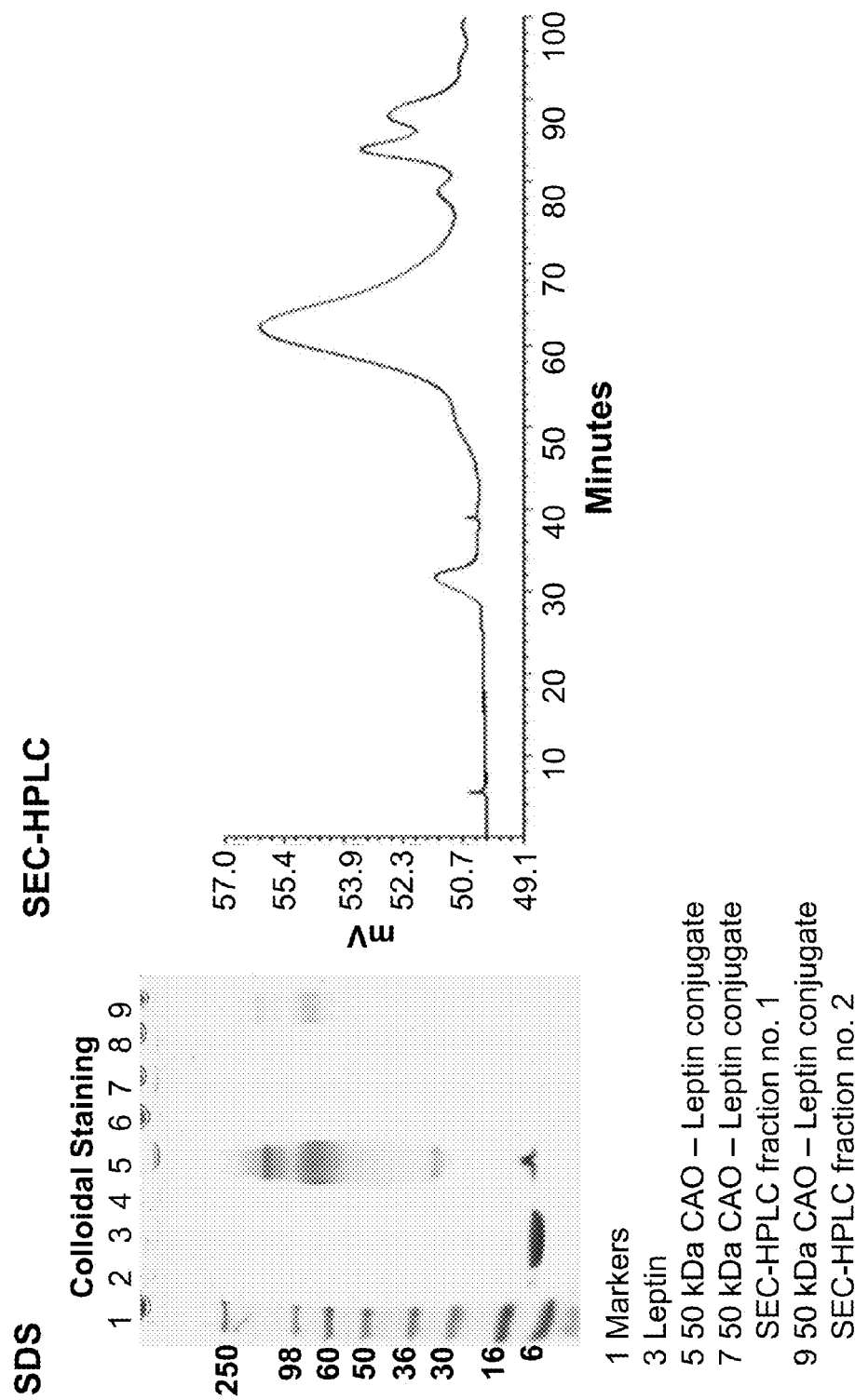
Figure. 4.1

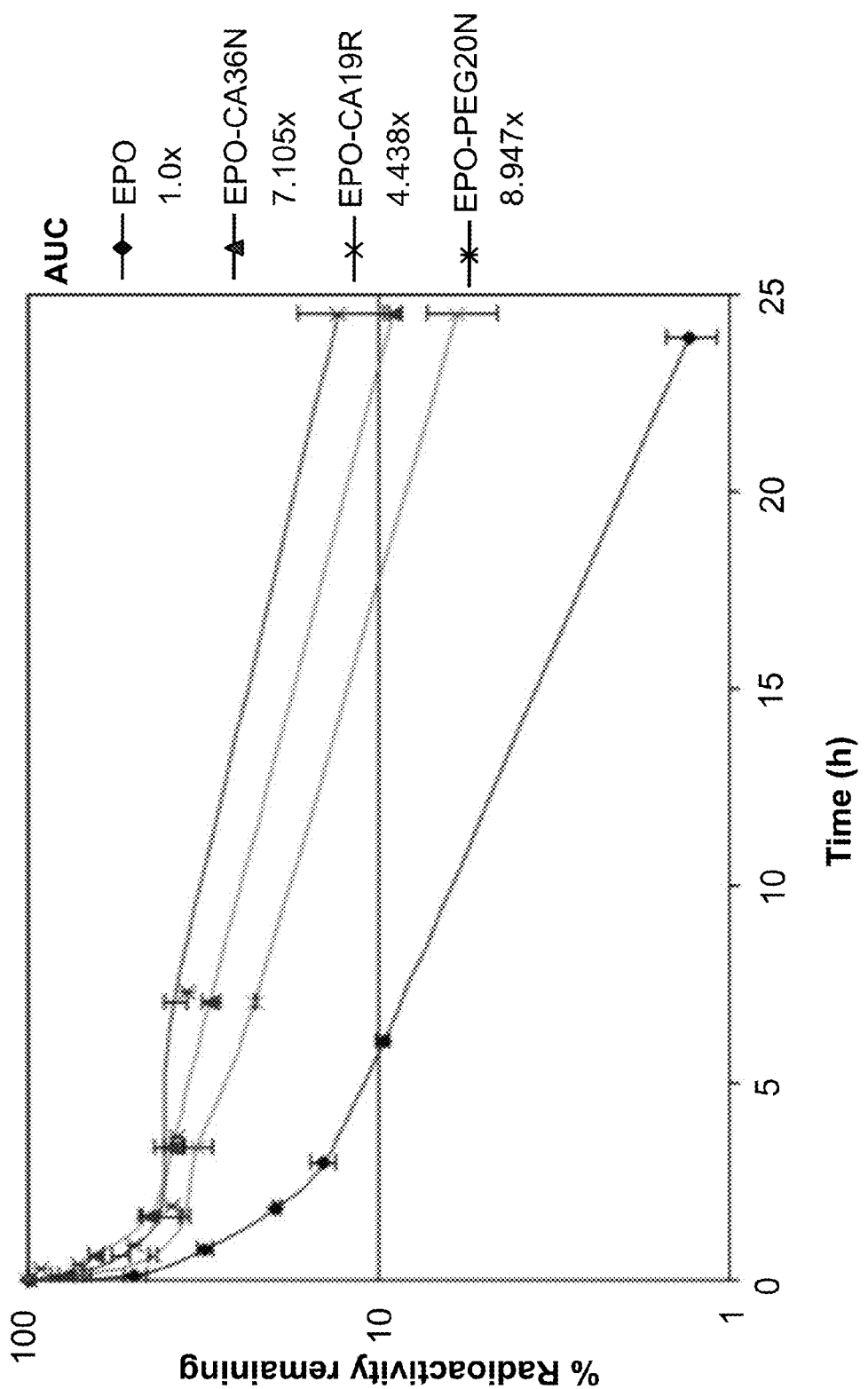
Figure 5.1

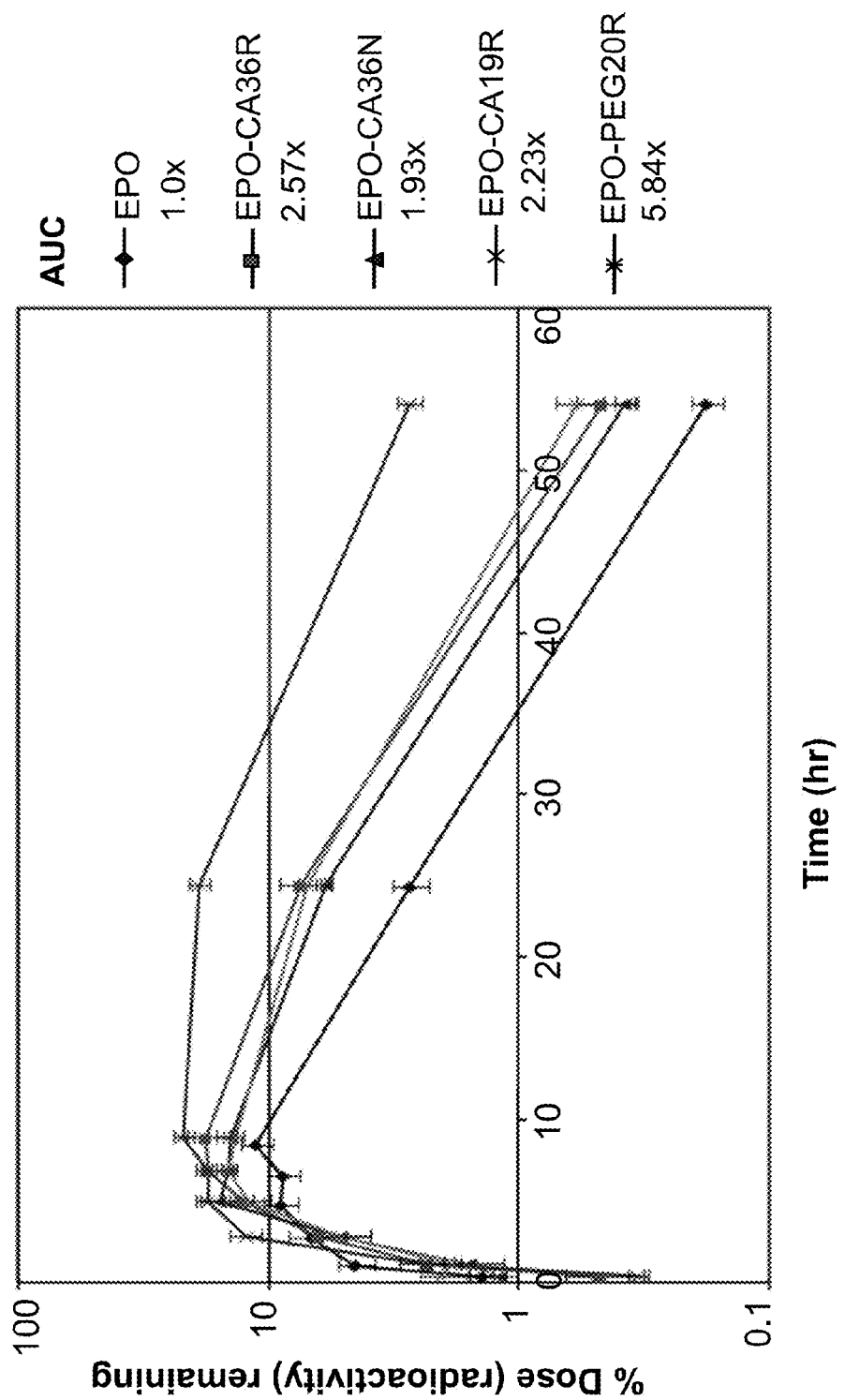
Figure 5.2

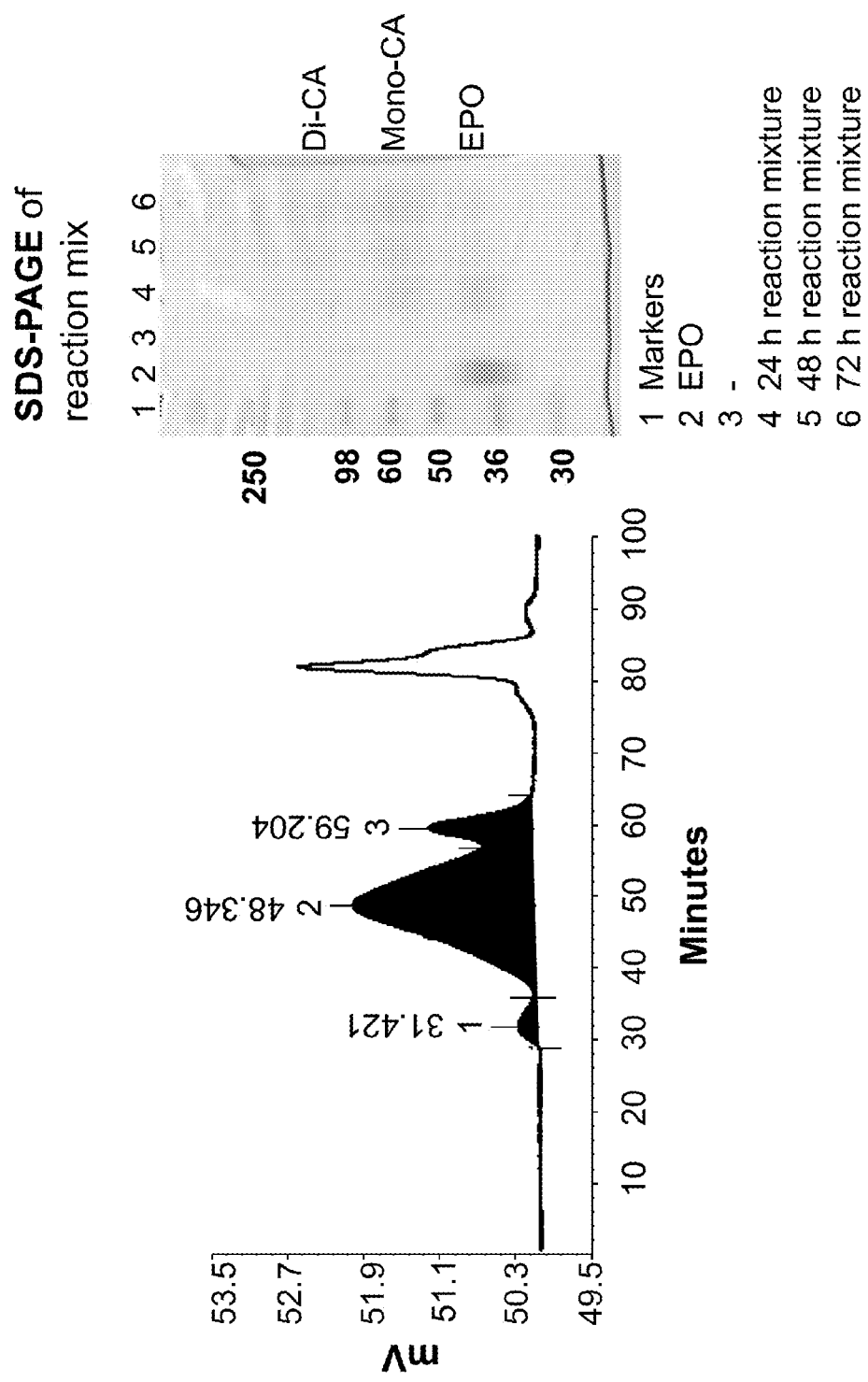
Figure 5.3

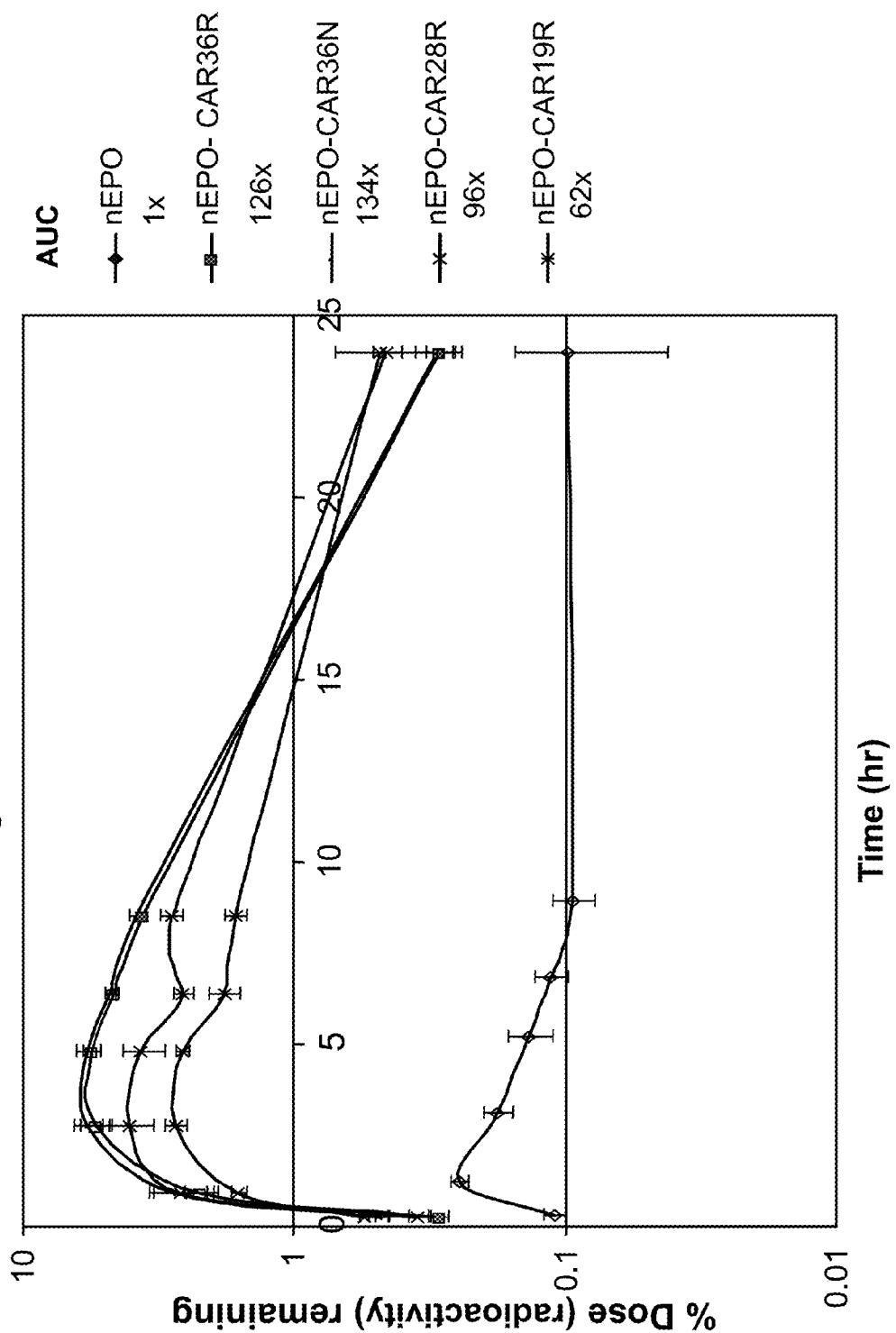

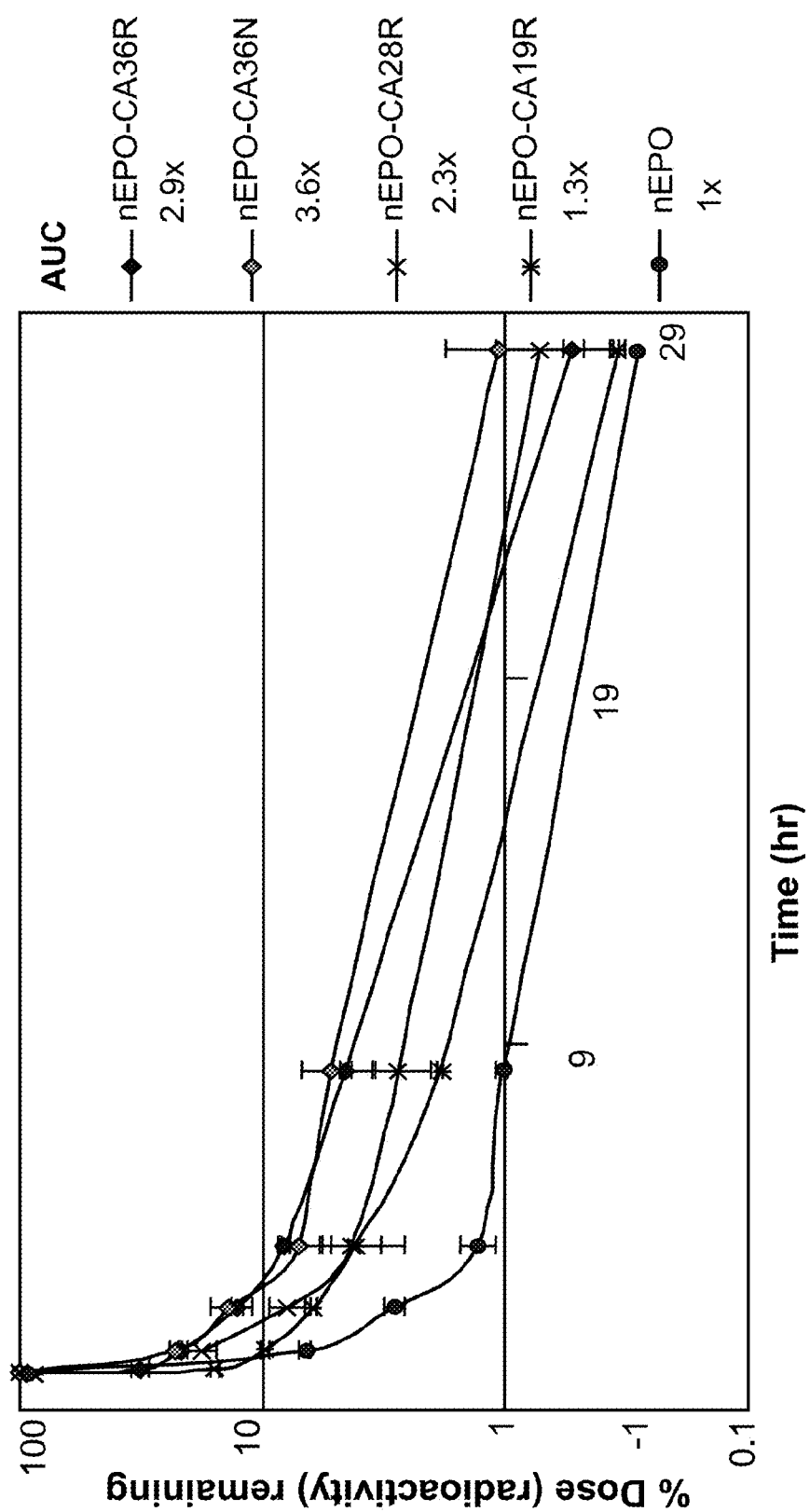
Figure 6.2

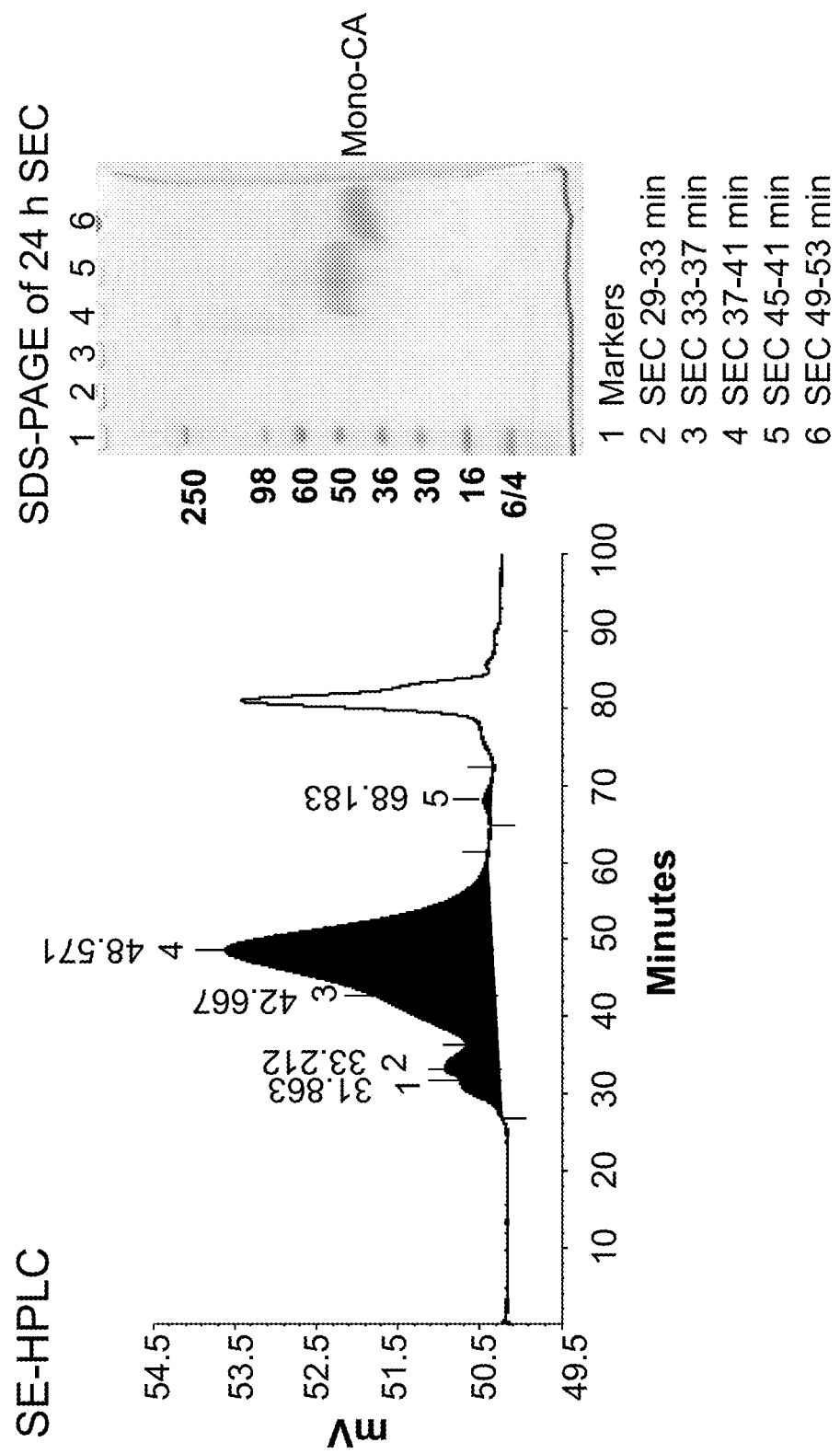
Figure 6.3

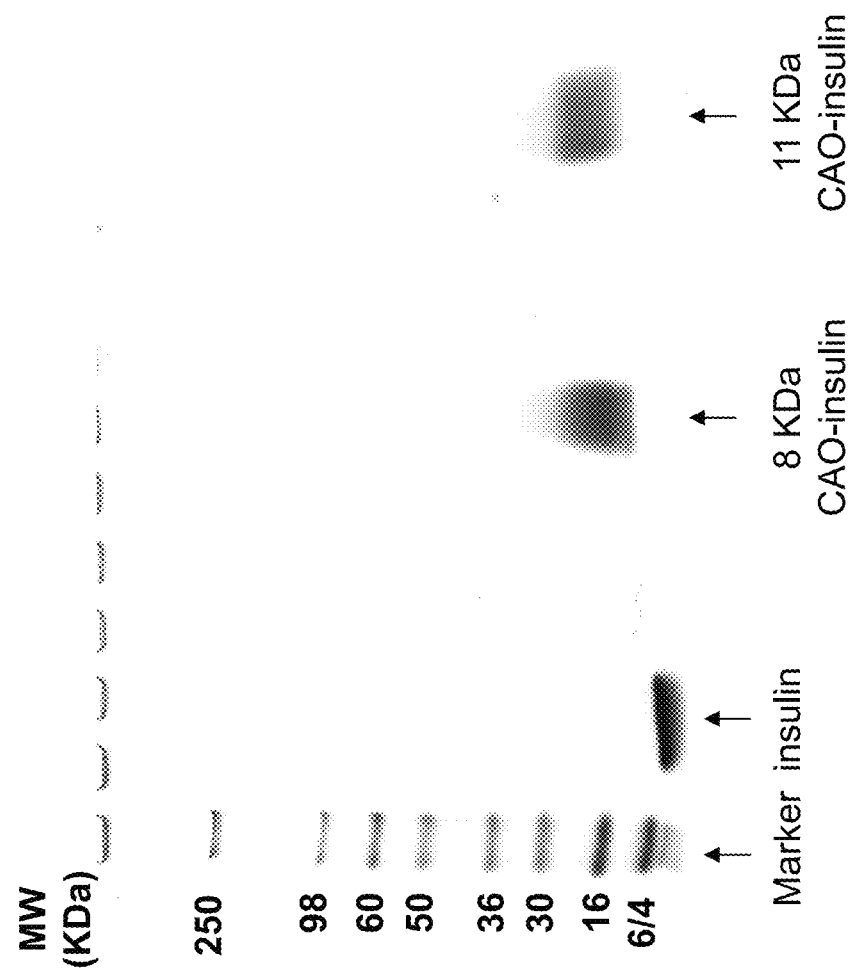
Figure 7.1

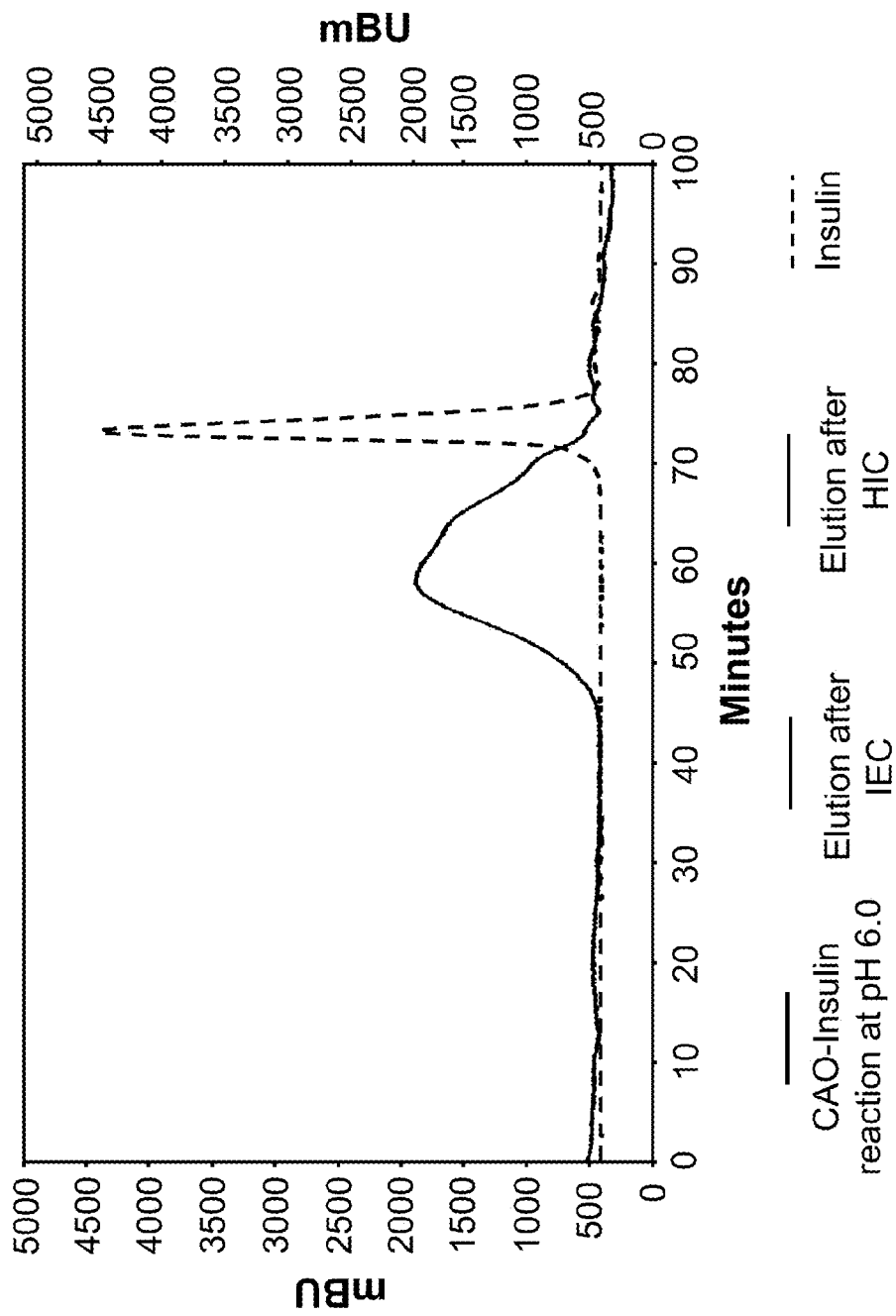
Figure 7.2

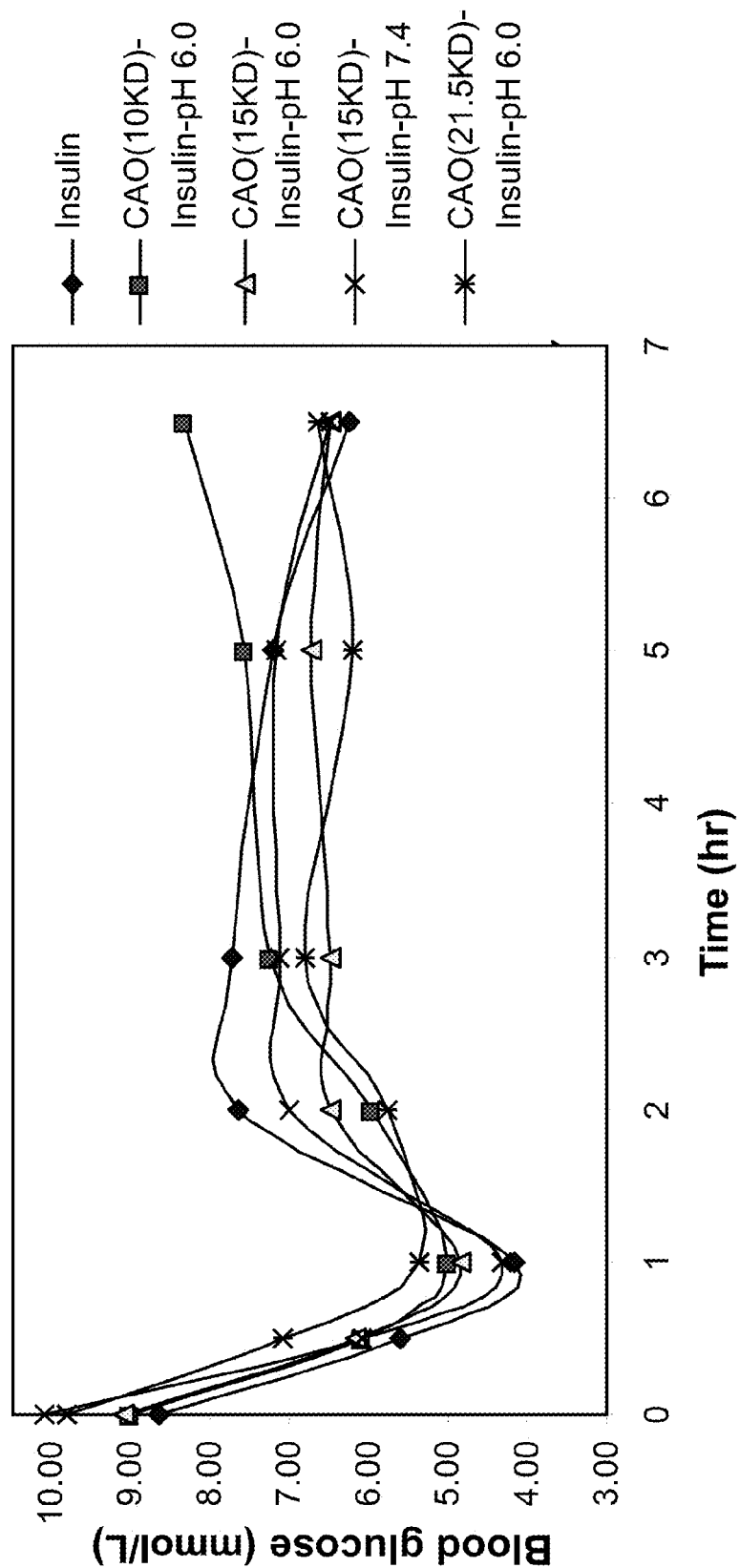
Figure 7.3

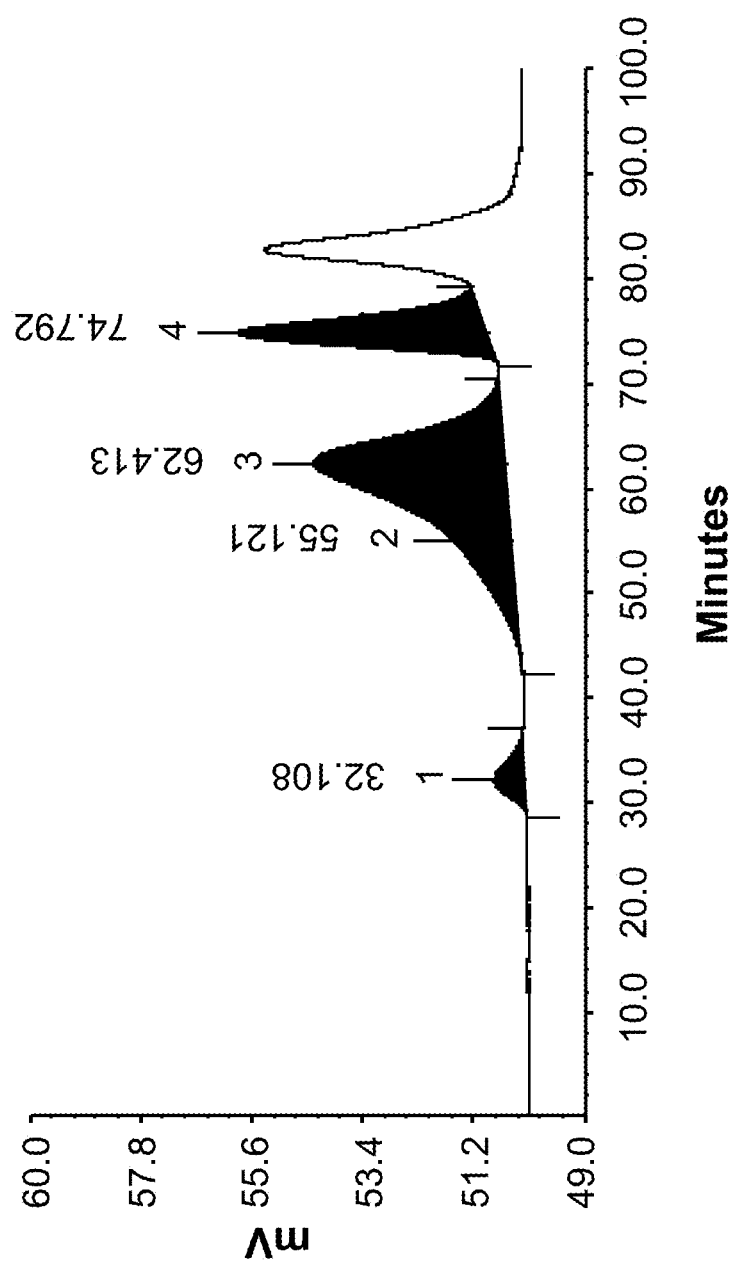
Figure 8.1

Figure 8.2
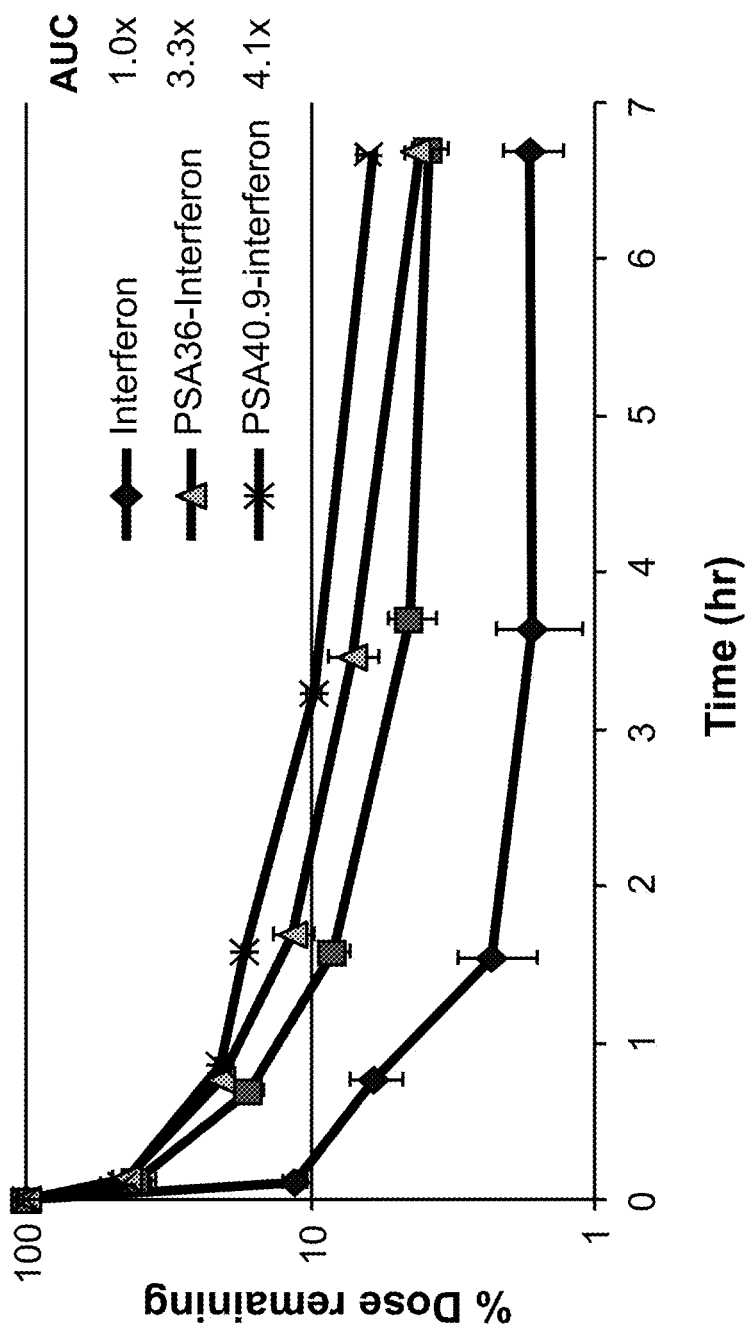

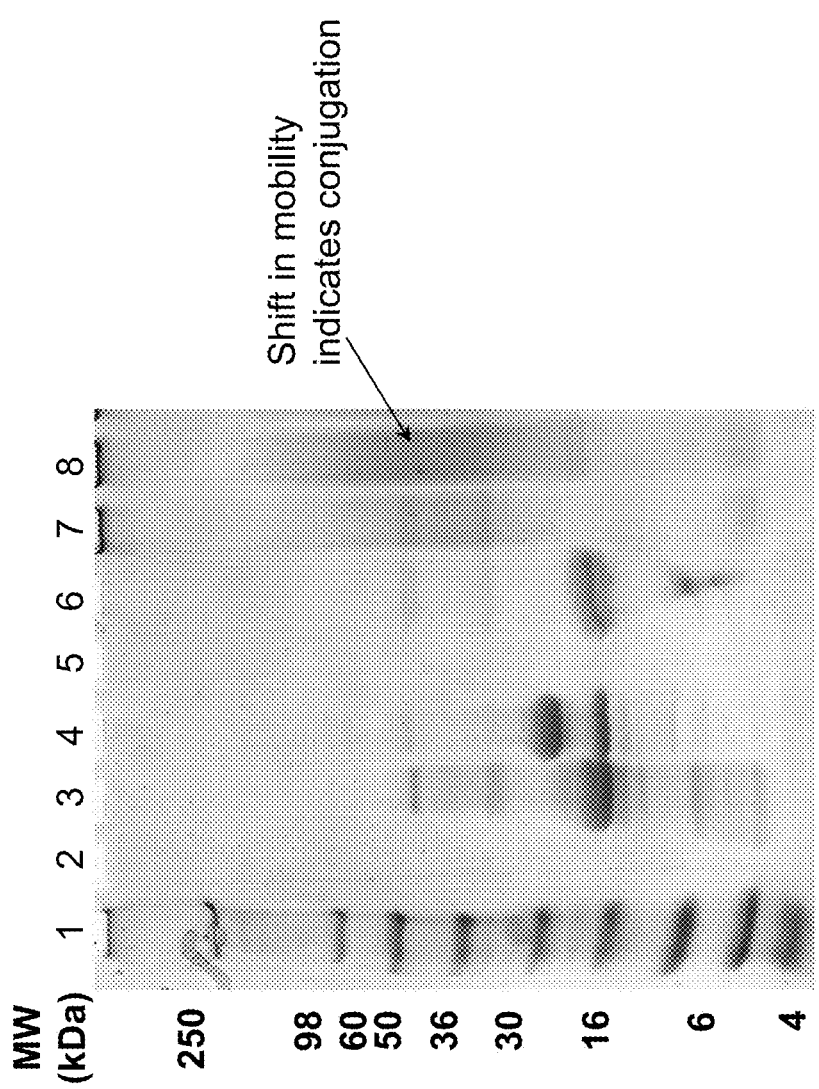
Figure 10.1

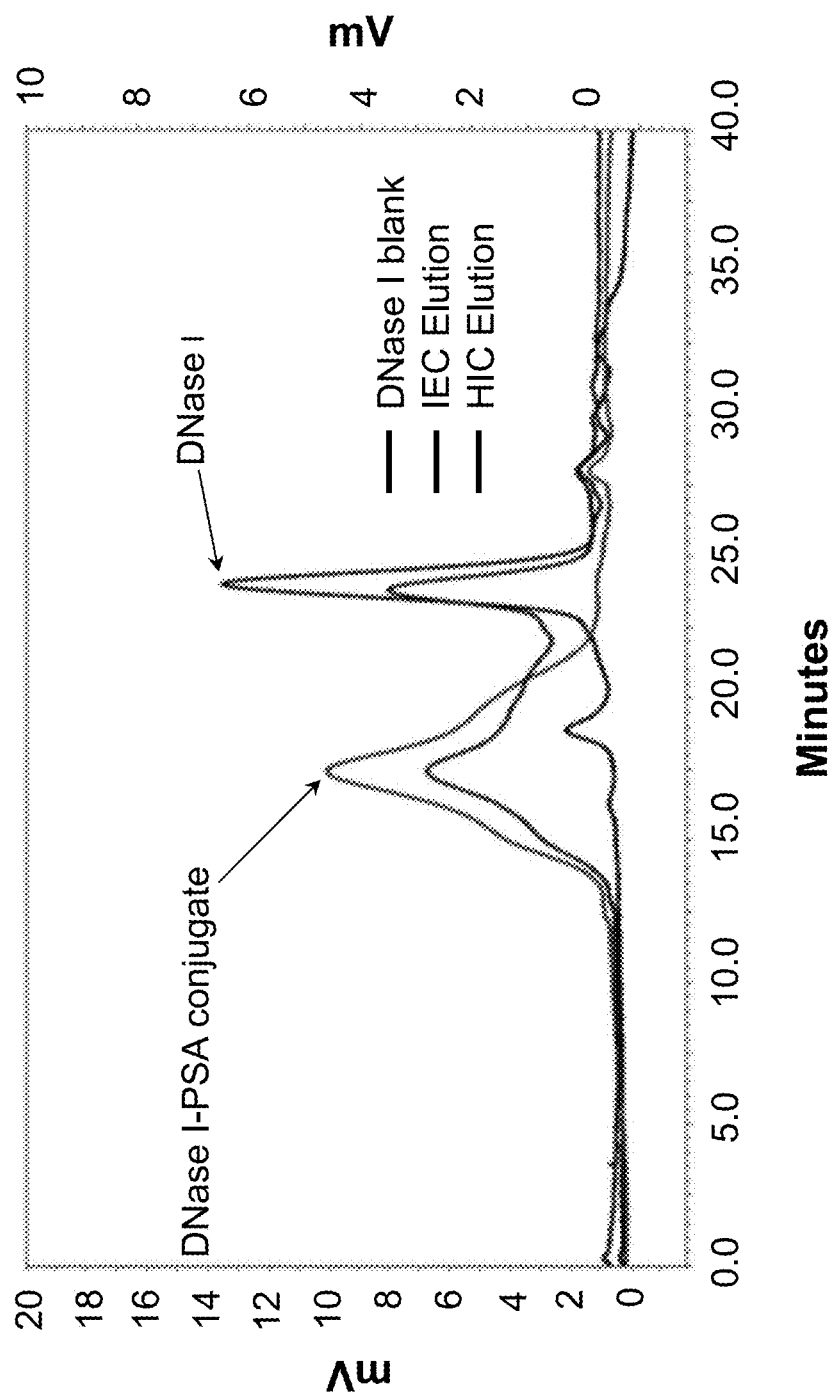
Figure 10.2

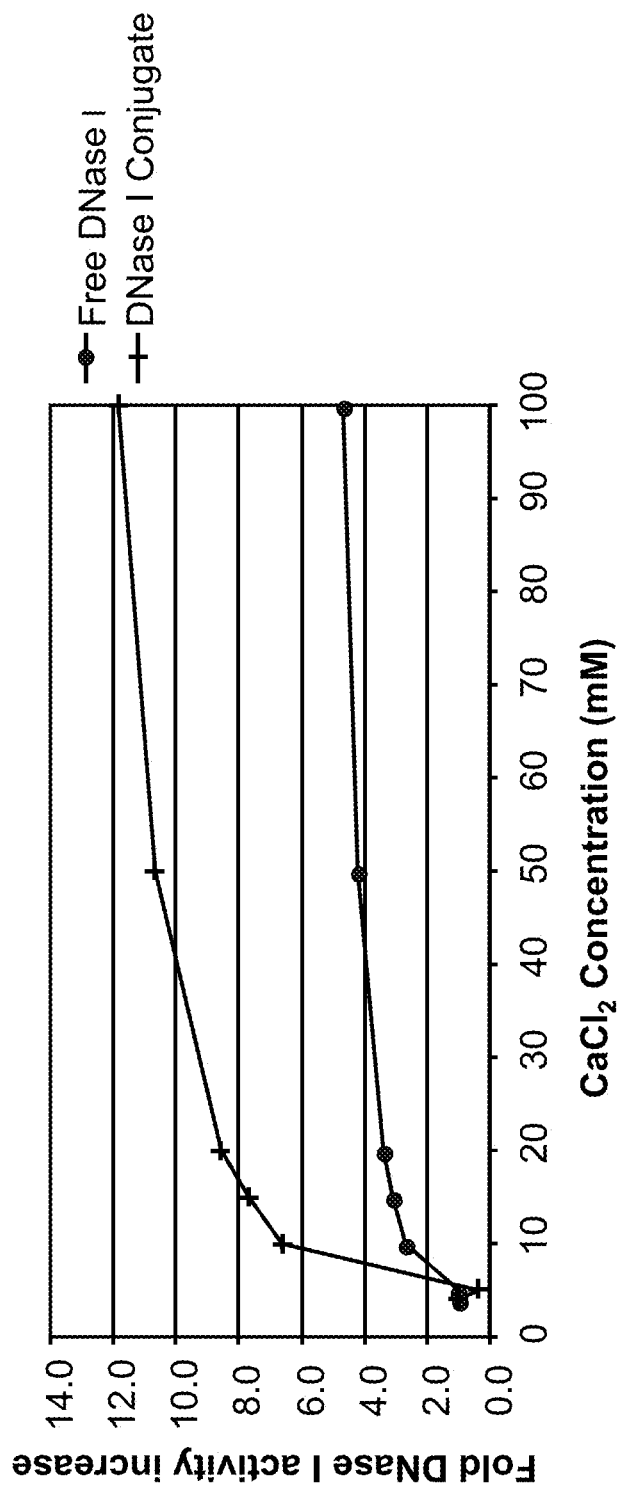
Figure 10.3

N-TERMINAL DERIVATISATION OF PROTEINS WITH POLYSACCHARIDES

The present application is a Continuation of U.S. Ser. No. 13/794,692 filed on Mar. 11, 2013, which is in turn a Continuation of U.S. Ser. No. 12/375,012, filed on Nov. 11, 2009, now issued as U.S. Pat. No. 8,394,921, which is in turn the National Stage Entry of International Application PCT/GB2007/002839, filed on Jul. 25, 2007, which claims priority to European Patent Application number 06117830.7, filed on Jul. 25, 2006, all of which are hereby expressly incorporated by reference in their entirety.

The present invention relates to methods for producing N-terminal derivatives of proteins in which a polysaccharide, preferably having at least terminal sialic units, and preferably consisting essentially only of sialic acid units, is reacted at the N-terminus of a protein or peptide under controlled conditions to produce an N-terminal derivative. The derivatives are useful for improving pharmacokinetics and pharmacodynamics of proteins and peptides.

Polysialic acids (PSAs) are naturally occurring unbranched polymers of sialic acid produced by certain bacterial strains and in mammals in certain cells. They can be produced in various degrees of polymerisation from n=about 80 or more sialic acid residues down to n=2 by limited acid hydrolysis or by digestion with neuraminidases, or by fractionation of the natural, bacterially derived forms of the polymer. In recent years, the biological properties of polysialic acids, particularly those of the alpha-2,8 linked homopolymeric polysialic acid, have been exploited to modify the pharmacokinetic properties of proteins and low molecular weight drug molecules. Polysialic acid derivatisation gives rise to dramatic improvements in circulating half-life for a number of therapeutic proteins including catalase and asparaginase, and also allows such proteins to be used in the face of pre-existing antibodies raised as an undesirable (and sometimes inevitable) consequence of prior exposure to the therapeutic protein [Fernandes and Gregoriadis, 2006; Jain et al., 2003, 2004]. The alpha-2,8 linked polysialic acid offers an attractive alternative to PEG, being an immunologically invisible biodegradable polymer which is naturally part of the human body, and which degrades, via tissue neuraminidases, to sialic acid, a non-toxic saccharide.

We have previously described methods for the attachment of polysaccharides to therapeutic agents such as proteins [U.S. Pat. No. 5,846,951; WO-A-0187922]. Some of these methods depend upon chemical derivatisation of the 'non-reducing' end of the polymer to create a protein-reactive aldehyde moiety which reacts at primary amine groups. A non-reducing sialic acid terminal unit, since it contains vicinal diols, can be readily (and selectively) oxidised with periodate to yield a mono-aldehyde form, which is much more reactive towards proteins, and which comprises a suitably reactive element for the attachment of proteins via reductive amination and other chemistries. The reaction is illustrated in FIG. 1 which A) shows the oxidation of colominic acid (alpha-2,8 linked polysialic acid from *E. coli*) with sodium periodate to form a protein-reactive aldehyde at the non-reducing end and B) shows the selective reduction of the Schiff's base with sodium cyanoborohydride to form a stable irreversible covalent bond with the protein amino group.

Due to the polyfunctional nature of proteins, PSA and PEG-conjugation strategies invariably lead to a mixture of chemically different molecular entities. Unintentional by-products may be generated during the conventional conjugation reactions described above by reaction of the colominic acid with side chains of amino acids, for instance. These may be sufficient to be troublesome in the manufacture of chemically defined conjugates required by regulatory authorities for therapeutic use in man and animals.

A site-directed approach of conjugating proteins to poly (ethylene glycol), which allows for the preparation of essentially homogeneous PEG-protein derivatives with a single PEG chain conjugated to the amine terminus of the protein is reported by Kinstler et. al., 2002. This selectivity is achieved by conducting the reductive alkylation of proteins with PEG-aldehydes at a lower pH than usual. However, the method was applied to conjugation with PEG only.

The rules for chemistry of PEGylation cannot be applied to polysialylation as such because of the difference in the physiochemical properties of these molecules. PSA is an acid labile polymer and is stable for weeks around neutral pH (FIG. 2.2). The results in FIG. 2.2 show that at pH 6.0 and 7.4 CA is stable for 8 days, at pH 5.0 there is slow degradation (after 48 hours 92% of initial MW), and at pH 4.0 there is slow degradation (after 48 hours 70% of initial MW). Polysialic acid is highly hydrophilic whereas PEG is an amphiphilic molecule in nature. When polysialylation is carried out using conditions used for PEGylation, aggregation and precipitation of the proteins is seen in many cases.

One of the most challenging tasks which remains in the development of protein pharmaceutical is dealing with physical and chemical instabilities of proteins. Protein pharmaceuticals usually have to be stored under cold conditions or be freeze-dried to achieve an acceptable shelf life. Excipients (for instance, stabilising buffers, sugars, polyols, surfactants, salts, PEG, polymers, metal ions and amino acids) and structural modification have been used to improve the stability of proteins giving them greater stability and shelf-life. There still exists a need to provide improved formulations of protein-PSA conjugates.

In accordance with a first aspect of the present invention we provide a method for producing a purified N-terminal derivative of a protein or peptide in which (i) a polysaccharide is reacted at the amine group of the N-terminus of a protein or peptide in aqueous acidic solution to produce an N-terminal derivative and (ii) the resultant N-terminal derivative is purified in aqueous solution of higher pH than in step (i).

In this invention we describe results of the application of a facile and scaleable chemical approach which has allowed us to prepare stoichiometrically defined, site-directed conjugates of polysaccharides, preferably polysialic acid (PSA) to the N-terminus of proteins. Typically this is via reductive alkylation with PSA-aldehydes in an aqueous environment. Conjugating the N-terminus is advantageous since it is thought that this minimises any undesirable interference between the polysaccharide and the remainder of the amino acid residues in the protein.

The method requires restoration to neutral pH soon after derivatisation, otherwise the polysaccharide is degraded substantially by exposure to the acidic environment of the derivatisation buffer. The method also requires use of controlled pH and optionally the presence of formulation additives during the reaction in order to prevent precipitation of the protein.

This invention allows well-defined, chemically homogeneous and efficacious conjugates of proteins to be synthesized, which have great utility in the pharmaceutical industry.

In this specification, the terms "protein" and "peptide" are used interchangeably.

The protein reacts mainly at the N-terminal amine group. This is achieved by the pH conditions of the reaction which selectively promote chemical reaction at the N-terminus of the protein. FIG. 2.1 shows derivatisation of a protein with PSA. Selective reduction of the Schiff's base with cyanoborohydride to form a stable irreversible covalent bond with the N terminal amino group is shown.

The aqueous acidic solution is the reaction medium in which the derivatisation reaction is carried out. This may be a buffer solution, for instance, sodium acetate. The reaction medium is water-based.

The method according to the first aspect of this invention requires that the purification step, step (ii), is carried out at a higher pH than the derivatisation step, step (i). Preferably, the purification step is carried out at substantially neutral pH. If the purification is performed at the same pH as the derivatisation step, which is acidic, the polysaccharide is likely to undergo degradation. By acidic pH, we mean a pH which is less than 7. Preferably, in step (i) of the method the pH of the aqueous acidic solution is in the range 3.0-6.5, more preferably in the range 4.0-6.0. The pH of the solution used in step (ii) of the method is less acidic than the pH of the solution in the first step. The pH is preferably substantially neutral and has a pH in the range 6.5-9.5, preferably 6.5-8.5, most preferably 6.5-8.0.

In one embodiment of this invention, the polysaccharide is activated prior to reaction with the protein or peptide to produce an activated derivative. Typically, the activated derivative of a polysaccharide has a reactive aldehyde group and step (i) is carried out under reducing conditions. Borohydride may be used to provide the reducing conditions. The N-terminus of the protein reacts with the reactive aldehyde group to produce an adduct which, when reduced, produces the N-terminal derivative of a protein or peptide.

The reactive aldehyde may be produced by selective oxidation of the polysaccharide using periodate.

The activation of polysaccharides should preferably be carried out under conditions such that there is substantially no mid-chain cleavage of the backbone of a long-chain (polymeric) starting material, that is substantially no molecular weight reduction. The activation step will typically be the provision of an aldehyde moiety at the terminus of the polysaccharide. Enzymes which are capable of carrying out this step may be used. Most conveniently the oxidation is a chemical oxidation. The reaction may be carried out with immobilised reagents such as polymer-based perrhuthenate. The most straightforward method is carried out with dissolved reagents. The oxidant is suitably perrhuthenate, or, preferably, periodate. Oxidation may be carried out with periodate at a concentration in the range 1 mM to 1M, at a pH in the range 3 to 10, a temperature in the range 0 to 60° C. for a time in the range 1 min to 48 hours.

Suitable reduction conditions for the derivatisation reaction may utilise hydrogen with catalysts or, preferably hydrides, such as borohydrides. These may be immobilised such as Amberlite (trade mark)-supported borohydride. Preferably alkali metal hydrides such as sodium borohydride is used as the reducing agent, at a concentration in the range 1 µM to 0.1M, a pH in the range 5.0 to 10, a temperature in the range 0 to 60° C. and a period in the range 1 min to 48 hours. The reaction conditions are selected such that pendant carboxyl groups on the starting material are not reduced. Other suitable reducing agents are cyanoborohydride under acidic conditions, e.g. polymer supported cyanoborohydride or alkali metal cyanoborohydride, L-ascorbic acid, sodium metabisulphite, L-selectride, triacetoxyborohydride etc.

Other activated derivatives of polysaccharides may have utility in the present invention, including those with pendant functional groups such as NHS, as described in our earlier patent application WO 06/00540.

Preferably, the polysaccharide is an anionic polysaccharide such as polysialic acid (PSA), heparin or chondroitin sulfate. Most preferably, the polysaccharide is PSA. However, in the invention this preferred polysaccharide starting material may comprise units other than sialic acid in the molecule. For instance sialic acid units may alternate with other saccharide units. Preferably, however, the polysaccharide consists substantially only of units of sialic acid. Preferably these are joined 2→8 and/or 2→9.

Preferably the polysaccharide starting material has at least 2, more preferably at least 5, more preferably at least 10, for instance at least 50, saccharide units. For instance a polysaccharide may comprise at least 5 sialic acid units.

The polysialic acid may be derived from any source preferably a natural source such as a bacterial source, e.g. *E. coli* K1 or K92, group B meningococci, or even cow's milk or N-CAM the sialic acid polymer may be a heteropolymeric polymer such as group 135 or group V of *N. meningitidis*.

The polysialic acid may be in the form of a salt or the free acid. It may be in a hydrolysed form, such that the molecular weight has been reduced following recovery from a bacterial source.

The polysaccharide, preferably polysialic acid may be material having a wide spread of molecular weights such as having a polydispersity of more than 1.3, for instance as much as 2 or more. Preferably the polydispersity of molecular weight is less than 1.3 or 1.2, more preferably less than 1.1, for instance as low as 1.01.

The purification of the N-terminal derivative in step (ii) of the method of the first aspect of the present invention may be carried out using a variety of methods known in the art. Examples of suitable purification methods include HIC (hydrophobic interaction chromatography), SEC (size exclusion chromatography), HPLC (high performance liquid chromatography) and AEX (anion exchange chromatography).

In the method of the present invention, the reactive aldehyde is preferably at the non-reducing end of the polysaccharide. However, the reactive aldehyde may also be provided at the reducing end of the polysaccharide. Chemistry suitable for preparing a polysaccharide with a reactive aldehyde at the reducing terminal of a polysaccharide is described in our earlier application WO 05/016974. The process involves a preliminary selective oxidation step followed by reduction and then further oxidation to produce a compound with an aldehyde at the reducing terminal and a passivated non-reducing end.

The present invention has particular utility for the production of derivatives of therapeutic proteins. The protein may be, for instance, obestatin, leptin, interferon, FSH, galactosidase or Dnase.

Formulation additives may be present in the aqueous solution in either or both of steps (i) and (ii) of the method according to the first aspect of the invention. By formulation additive we mean an excipient which is capable of stabilising the protein or peptide either internally or externally, as described in Wang et al (1999). The excipient may be a stabiliser, a solubilser or a metal ion. Suitable examples of formulation additives include one or more buffers, stabilisers, surfactants, salts, polymers, metal ions, sugars, polyols or amino acids. These may be used alone or in combination.

Stabilisers typically act by destabilisation of the denatured state of a protein leading to increased Gibbs free energy change for unfolding of the protein. The stabiliser is preferably a sugar or a polyol, for example sucrose, sorbitol, trehalose, glycerol, mannitol, lactose and ethylene glycol. A stabilising buffer is sodium phosphate.

The solubiliser is preferably a surfactant, preferably a non-ionic surfactant. Suitable examples include Tween 80, Tween 20, Tween 40, Pluoronic F68, Brij 35 and Triton X100.

The metal ion is preferably divalent. Suitable metal ions include $Zn^{2+}$, $Ni^{2+}$, $Co^{2+}$, $Sr^{2+}$, $Cu^{2+}$, $Ca^{2+}$, $Mg^{2+}$ and $Fe^{2+}$.

The formulation additive may also be a polymer selected from PSA, PEG or hydroxy-beta-cyclodextrin.

Suitable amino acids and amino acid derivatives for use as the formulation additive include histidine, glycine, other similar amino acids and sodium aspartate.

A population of polysialic acids having a wide molecular weight distribution may be fractionated into fractions with lower polydispersities, i.e. into fractions with differing average molecular weights. Fractionation is preferably performed by anion exchange chromatography, using for elution a suitable basic buffer, as described in our earlier patent applications WO 2005/016794 and WO 2005/03149. The fractionation method is suitable for a polysialic acid starting material as well as to the derivatives. The technique may thus be applied before or after the essential process steps of this invention. Preferably, the resultant polysialic acid derivative has a polydispersity of less than 1.1.

In accordance with a second aspect of this invention we provide a composition comprising a population of polysialic acid derivatives of a protein, wherein the derivatives comprise between 2 and 200 sialic acid units and wherein the population consists substantially only of N-terminal derivatives of the protein.

By population we mean that there is more than one polysialic derivative in the composition. The derivatives may comprise the same or different numbers of sialic acid units. Preferably, the polydispersity of the polysialic acid in the composition is less than 1.3, more preferably less than 1.1.

In the population, substantially all of the protein is derivatised at the N-terminal amine only. By this, we mean that at least 85%, preferably at least 90%, most preferably at least 95% of the protein in the population is derivatised with PSA at the N-terminal amine only. The degree of derivatisation at the N-terminus can be measured using techniques well known in the art, such as peptide mapping and Edman Degradation.

The protein may be any protein which has a therapeutic use, for instance, obestatin, leptin, interferon, FSH, galactosidase or Dnase.

When the protein is FSH the derivatives typically comprise 75-200 sialic acid units.

When the protein is alpha-galactosidase the derivatives typically comprise 20-150 sialic acid units.

When the protein is DNase the derivatives typically comprise 2-120 sialic acid units.

When the protein is IFN the derivatives typically comprise 80-180 sialic acid units. The preferred polysialic acids are as detailed above for the other aspects of this invention.

The polysialic acid may be linked to the protein directly, i.e. as shown in FIG. 1, or via a linker. Suitable linkers are derived from N-maleimide, vinylsulphone, N-iodoacetamide, orthopyridyl or N-hydroxysuccinimide-functional group-containing reagents. The linker may also be biostable or biodegradable and comprise, for instance, a polypeptide or a synthetic oligomer. The linker may be derived from a bifunctional-group containing reagent, as further described in WO 2005/016973. A suitable bifunctional reagent is, for instance, Bis-NHS. The reagent may have general formula $Z-R^1-Z$ wherein each Z is a functional group and may be the same or different and $R^1$ is a bifunctional organic radical. Preferably, $R^1$ is selected from the group consisting of alkanediyl, arylene, alkarylene, heteroarylene and alkylheteroarylene, any of which may be substituted and/or interrupted by carbonyl, ester, sulfide, ether, amide and/or amine linkages. Particularly preferred is $C_3$-$C_6$ alkanediyl. Most preferably, $R^1$ corresponds to the appropriate portion of the suitable bifunctional reagent The polysialic acid derivatives may have general formula (I)

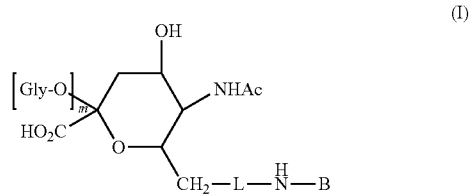

wherein m is at least one;
HNB is derived from $B-NH_2$ which is the N-terminal amine of the protein;
L is a bond, a linking group, or comprises a polypeptide or a synthetic oligomer;
GlyO is a sialic acid unit;
wherein the linking group, if present, is of general formula $-Y-C(O)-R^1-C(O)-$
wherein Y is $NR^2$ or $NR^2-NR^2$ and $R^1$ is a difunctional organic radical as defined above; and $R^2$ is H or $C_{1-6}$ alkyl.

In this aspect of the invention the protein is linked to the non-reducing end of the polysaccharide.

When the protein is attached directly to the polysaccharide, the group L is a bond. However, the group L may alternatively be derived from an N-maleimide, vinylsulphone, N-iodoacetamide, orthopyridyl or N-hydroxysuccinimide containing reagent. The reagent may have general formula $Z-R^1-Z$ as defined above. In this embodiment, L is typically a group

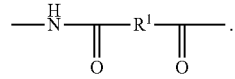

Compositions comprising the polysialic acid derivatives and a diluent as well as pharmaceutical compositions comprising novel compounds which have biological activity, and a pharmaceutically acceptable excipient also form part of the invention. Pharmaceutical compositions may be administered orally, intravenously, intraperitoneally, intramuscularly, subcutaneously, intranasally, intradermally, topically or intratracheally for human or veterinary use.

The compositions may further comprise a formulation additive, as detailed above.

A final aspect of the invention is an N-terminal derivative of a protein or peptide which is obtainable by a method according to the first aspect of this invention. Any of the preferred features of the derivatives discussed above are also applicable to this aspect of the invention.

The derivatisation of proteins and peptides etc. may result in increased half life, improved stability, reduced immunogenicity, and/or control of solubility and hence bioavailability and pharmacokinetic properties, or may enhance solubility of actives or viscosity of solutions containing the derivatised active. The new method is of particular value for creation of a monopolysialylated-protein conjugates. It is based on an understanding that at lower pHs N-terminal amine groups are more protonated and hence highly reactive.

The invention is illustrated by Examples 1-10 and by reference to the following drawings:—

Figure 9:
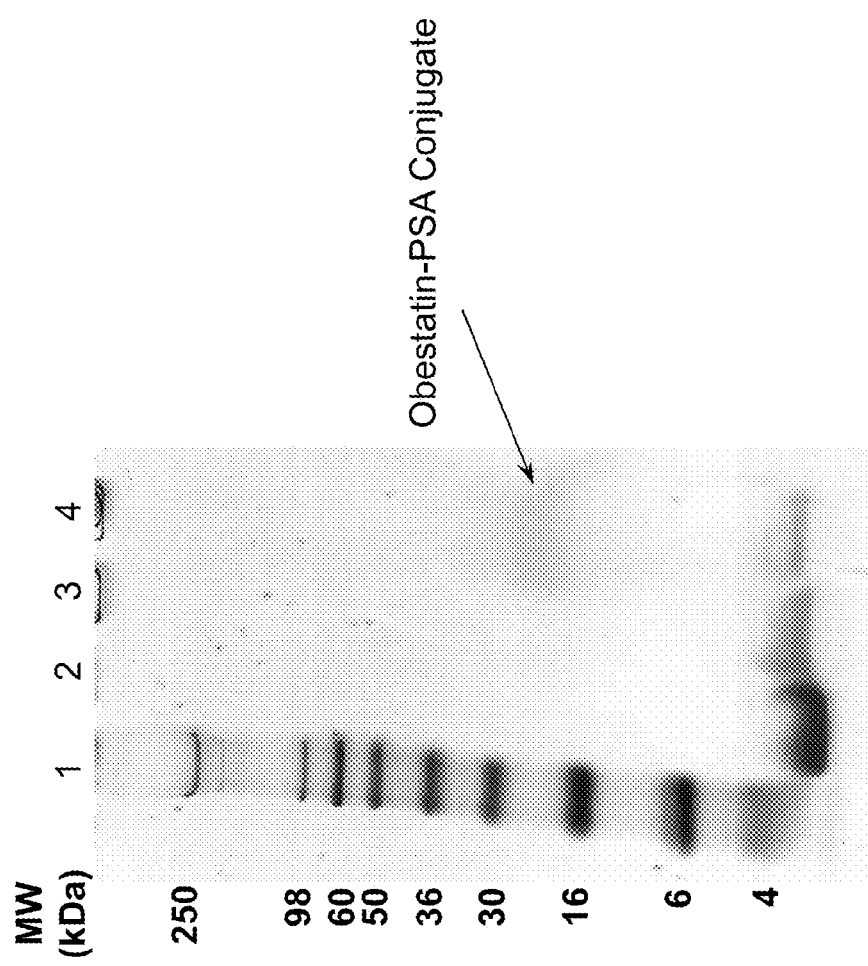

FIG. 2.1 is a reaction scheme showing the N-terminal derivatization of proteins;

FIG. 2.2 shows the degradation of colominic acid (CA) at different pHs using Triple Detection GPC (Viscotek: RI+RALS+Viscosiometer);

FIG. 3.1 illustrates the characterisation of GCSF-CA conjugates by SE-HPLC and SDS-PAGE;

FIG. 4.1 shows the SDS-PAGE and SE-HPLC of 50 kDa CAO-leptin conjugate;

FIG. 5.1 shows the in vivo clearance of EPO formulations (i.v);

FIG. 5.2 shows further in vivo clearance of EPO formulations (s.c);

FIG. 5.3 is the characterisation of EPO-CA conjugates by SE-HPLC and SDS-PAGE;

FIG. 6.1 illustrates the in vivo clearance of non-glycosylated EPO versus polysialylated non-glycosylated EPO (n=3-4+/−; s.c);

FIG. 6.2 illustrates further in vivo clearance of non-glycosylated EPO versus polysialyated EPO (i.v.; n=3-4+/− SEM);

FIG. 6.3 is the characterisation of NGEPO-CA conjugates by SE-HPLC and SDS-PAGE;

FIG. 7.1 is the characterisation of CA-insulin conjugates by SDS-PAGE (Tris-glycine (4-20%) gel);

FIG. 7.2 is the characterisation of purified CAO-insulin conjugates by SE-HPLC;

FIG. 7.3 shows the in vivo efficacy of CAO-insulin formulations (0.3 U s.c.; n=4) to outbred female mice; ~25 grams;

FIG. 8.1 shows the SE-HPLC of polysialylation of Interferonalpha2b (CA 39 kDa reaction mixture after 24 hours);

FIG. 8.2 shows the in vivo clearance of polysialylated interferon (i.v.; n=4+/−SEM);

FIG. 9 is an SDS-PAGE of conjugates obestatin;

FIG. 10.1 shows SDS PAGE of the conjugates in Example 10.4;

FIG. 10.2 is a SE-HPLC of the conjugates in Example 10.5; and

FIG. 10.3 is a graph showing Dnase I Activity vs calcium chloride concentration.

EXAMPLES

Materials

Ammonium carbonate, ethylene glycol, polyethylene glycol (8 KDa), sodium cyanoborohydride (>98% pure), sodium meta-periodate and molecular weight markers were obtained from Sigma Chemical Laboratory, UK. The colominic acid used, linear α-(2→8)-linked *E. coli* K1 polysialic acids (22.7 kDa average, high polydispersity 1.34, 39 kDa p.d. 1.4; 11 kDa, p.d. 1.27) was from Camida, Ireland, radioactive iodide ($Na^{125}I$) was purchased from Amersham, UK. Other materials included 2,4 dinitrophenyl hydrazine (Aldrich Chemical Company, UK), dialysis tubing (3.5 KDa and 10 KDa cut off limits; Medicell International Limited, UK), Sepharose SP HiTrap, PD-10 columns (Pharmacia, UK), Tris-glycine polyacrylamide gels (4-20% and 16%), Tris-glycine sodium dodecylsulphate running buffer and loading buffer (Novex, UK). Deionised water was obtained from an Elgastat Option 4 water purification unit (Elga Limited, UK). All reagents used were of analytical grade. A plate reader (Dynex Technologies, UK) was used for spectrophotometric determinations in protein or CA assays. B6D2F1 mice (7-8 weeks old; 20 g body weight) were purchased from Harlan, UK and acclimatized for at least one week prior to their use.

Ammonium sulphate, GCSF (SII, india), sorbitol, Tween 20, Q FF [column 1 ml or 5 ml; Amersham Biosciences, UK], sodium chloride, sodium phosphate, Hitrap Butyl HP column [1 or 5 ml; Amersham Biosciences, UK], mouse leptin recombinant (Biomyx), Erythropoietin (EPO) and non-glycosylated EPO (NGEPO) (m.w. 30600; SIIL, India), Tris [Sigma, UK], Sodium Acetate [BDH, UK], Sodium Phosphate [BDH, UK], Insulin (Sigma, UK).

1. Protein and Colominic Acid Determination

Quantitative estimation of polysialic acids (as sialic acid) with the resorcinol reagent was carried out by the resorcinol method [Svennerholm, 1957] as described elsewhere [Gregoriadis et al., 1993; Fernandes and Gregoriadis, 1996, 1997]. Protein was measured by the BCA colorimetric method or UV absorbance at 280 nm.

2.1 Activation of Colominic Acid

Freshly prepared 0.02 M sodium metaperiodate ($NaIO_4$) solution (8 fold molar excess) was mixed with CA at 20° C. and the reaction mixture was stirred magnetically for 15 min in the dark. A two-fold volume of ethylene glycol was then added to the reaction mixture to expend excess $NaIO_4$ and the mixture left to stir at 20° C. for a further 30 min. The oxidised colominic acid was dialysed (3.5 KDa molecular weight cut off dialysis tubing) extensively (24 h) against a 0.01% ammonium carbonate buffer (pH 7.4) at 4° C. Ultrafiltration (over molecular weight cut off 3.5 kDa) was used to concentrate the CAO solution from the dialysis tubing. Following concentration to required volume, the filterate was lyophilized and stored at −40° C. until further use. Alternatively, CA was recovered from the reaction mixture by precipitation (twice) with ethanol.

2.2 Determination of the Oxidation State of CA and Derivatives

Qualitative estimation of the degree of colominic acid oxidation was carried out with 2,4 dinitrophenylhydrazine (2,4-DNPH), which yields sparingly soluble 2,4 dinitrophenyl-hydrazones on interaction with carbonyl compounds. Non-oxidised (CA)/oxidised (CAO) were added to the 2,4-DNPH reagent (1.0 ml), the solutions were shaken and then allowed to stand at 37° C. until a crystalline precipitate was observed [Shriner et. al., 1980]. The degree (quantitative) of CA oxidation was measured with a method [Park and Johnson, 1949] based on the reduction of ferricyanide ions in alkaline solution to ferric ferrocyanide (Persian blue), which is then measured at 630 nm. In this instance, glucose was used as a standard.

2.3 Gel Permeation Chromatography

Colominic acid samples (CA, and CAO) were dissolved in $NaNO_3$ (0.2M), $CH_3CN$ (10%; 5 mg/ml) and were chromatographed on over 2×GMPW$_{XL}$ columns with detection by refractive index (GPC system: VE1121 GPC solvent pump, VE3580 RI detector and collation with Trisec 3 software Viscotek Europe Ltd. Samples (5 mg/ml) were filtered over 0.45 μm nylon membrane and run at 0.7 cm/min with 0.2M NaNO$_3$ and CH$_3$CN (10%) as the mobile phase.

Results

Figure 1A:
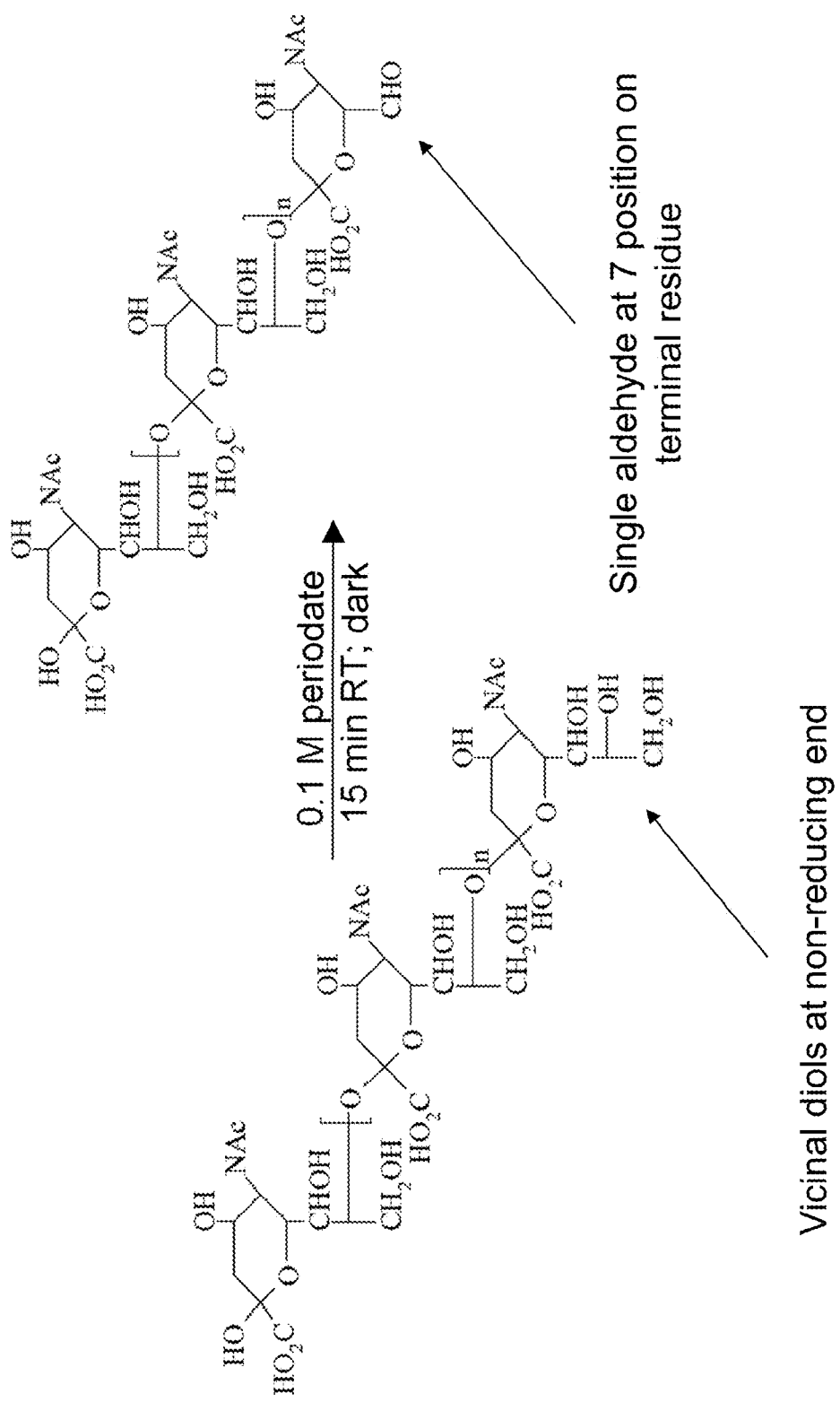
FIG. 1a is a reaction scheme showing the prior art activation of the non-reducing sialic acid terminal unit.
Figure 1B:
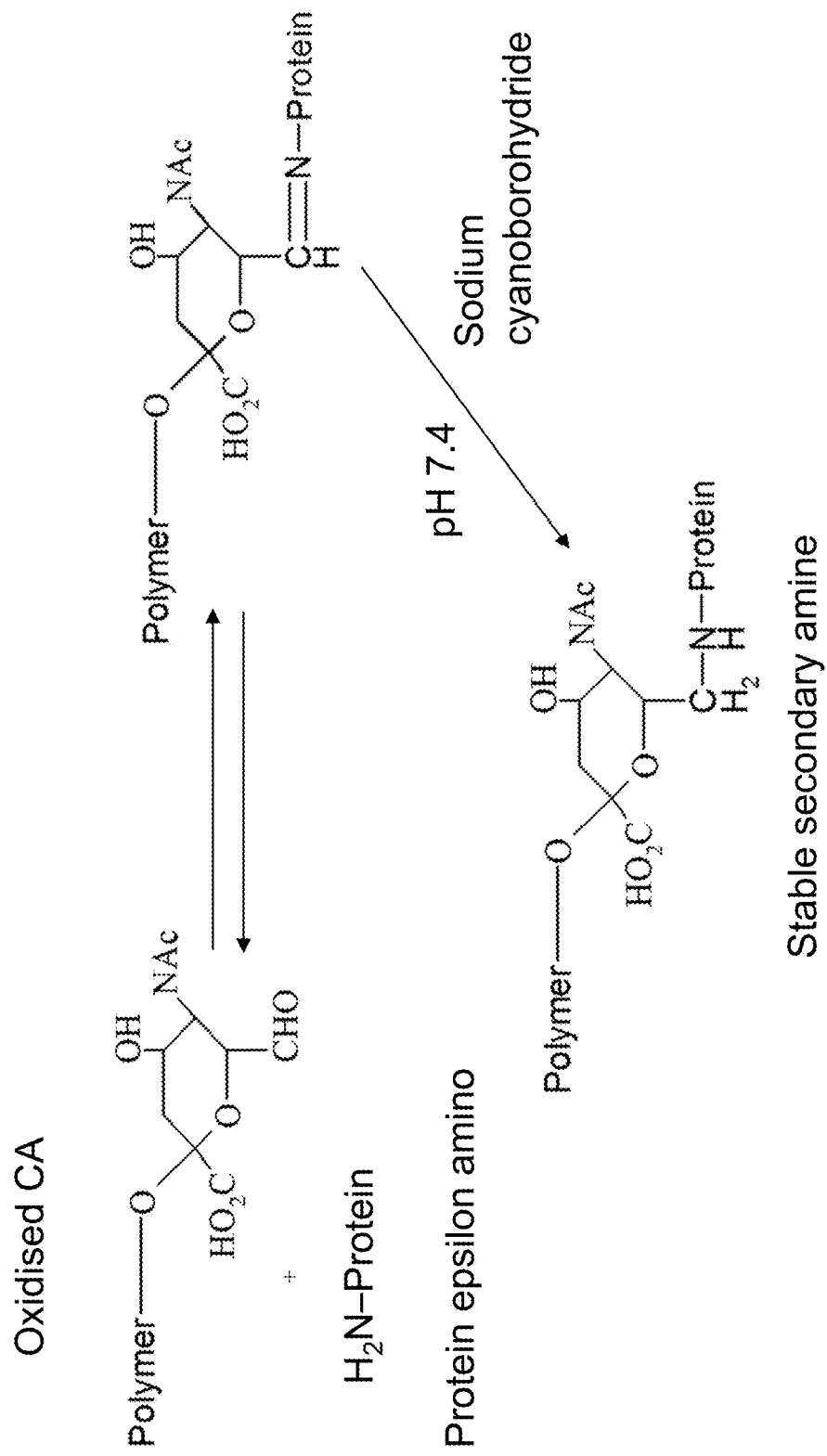
FIG. 1b is a reaction scheme showing the prior art reductive amination of the aldehyde moiety of the product of reaction scheme 1a using a protein-amine moiety.

Colominic acid (CA), a polysialic acid, is a linear alpha-2,8-linked homopolymer of N-acetylneuraminic acid (Neu5Ac) residues (FIG. 1a). Exposure of colominic acids to oxidation [Lifely et. al., 1981] was carried out for 15 min using 20 mM periodate at room temperature. The integrity of the internal alpha-2,8 linked Neu5Ac residues post periodate treatment was analysed by gel permeation chromatography and the chromatographs obtained for the oxidised (CAO), material was compared with that of native CA. It was found that oxidized and native CA exhibit almost identical elution profiles, with no evidence that the successive oxidation step give rise to significant fragmentation of the polymer chain.

Quantitative measurement of the oxidation state of CA was performed by ferricyanide ion reduction in alkaline solution to ferrocyanide (Prussian Blue) [Park and Johnson, 1949] using glucose as a standard. Table 1 shows that the oxidized colominic acid was found to have a greater than stoichiometric (>100%) amount of reducing agent, i.e. 112 mol % of apparent aldehyde content comprising the combined reducing power of the reducing end hemiketal and the introduced aldehyde (at the other end).

TABLE 1

Degree of oxidation of various colominic acid intermediates in the double oxidation reaction scheme using glucose as a standard (100%, 1 mole of aldehyde per mole of glucose; n = 3 ± s.d).

| CA species | Degree of oxidation |
|---|---|
| colominic acid (CA) | 16.1 ± 0.63 |
| colominic acid-oxidised (CAO) | 112.03 ± 4.97 |
| colominic acid-reduced (CAOR) | 0; Not detectable |
| colominic acid-oxidised-reduced-oxidised (CAORO) | 95.47 ± 7.11 |

3. Preparation of N-Terminal Protein-CA Conjugates with Formulation Additives 3.1 Preparation of GCSF-CA Conjugates G-CSF (18.8 kDa) was supplied as a solution (1.05 mg/ml in 10 mM sodium acetate buffer, pH 4.0 containing 5% sorbitol, 0.025 mg/ml polysorbate 80) and stored at 2-8° C. The required amount of GCSF was taken into an eppendorf and placed on ice. The amount of CA (e.g. oxidised or non-oxidised CA 11 molar excess over protein) to be added for conjugation was calculated based on formula:

$$\text{Weight of } CA = \frac{\text{Amount of protein (g)}}{(\text{MW of protein})} \times (\text{MW of } CA) \times (\text{Molar excess of } CA)$$

Required amount of CA was weighed out. CA was solubilised in 10 mM NaOAc, 5% sorbitol, pH 5.5 (20% volume of the final reaction volume was used here), gently vortexed the mixture until all the CA has dissolved and then either filtered into a new eppendorf or centrifuged at 4000 rpm for 5 min and the supernatant was transferred to a new eppendorf to remove any aggregated/precipitated material. Required volume of 10 mg/ml Tween 20 stock solution was added, in order to have a final concentration of 0.5 mg/ml of the Tween 20 in the final reaction mixture. Required amount of G-CSF protein solution was added to the CA solution to give a 11 molar excess (for 40 kDa) of CA and gently mixed by keeping the reaction mixture on a gentle shaker at 4±1° C. 100 mg/ml NaCNBH$_3$ solution was added in order to have 50 mM or 3.17 mg/ml in the final reaction mixture, gently mixed and pH of the final reaction mixture was checked, if necessary adjusted the pH to 5.5 with 1 M NaOH/HCl at 4±1° C. Finally adjusted the volume of the reaction using 10 mM NaOAc, 5% sorbitol, pH 5.5 to give a protein concentration of 0.67 mg/ml in the reaction mixture. Tube was sealed and stirred at desired temperature (4±1° C.) for 24 hours. The reaction was stopped by an appropriate method and samples were taken out for in vitro activity assay on MNFS 60 cell, SDS-PAGE (using 4-20% Tris glycine gel), SE-HPLC; superose 6 column) & checked the pH of reaction mixture. To eliminate any precipitate the reaction mixture was centrifuged at 13000 rpm for 5 min before SE-HPLC analysis and purification, preferred buffer for SE-HPLC was 0.1 M Na phosphate (pH 6.9).

3.2 Purification and Characterization of GCSF-CA Conjugates

The remaining reaction mixture sample was diluted with AEX buffer A (20 mM Sodium acetate, 50 mM Sodium chloride pH 5.0) (1.5 ml reaction mixture+9 ml of buffer A) pH was checked and adjusted if required to pH 5.0, loaded on the AEX column previously equilibrated with AEX buffer A. The loading fractions were collected and labelled. The column was washed with AEX buffer A (at least 5 column volume), fractions collected (each fraction 1.5 column volume) and labelled. Eluted the product with AEX buffer B (50 mM sodium phosphate, 0.65M Sodium Chloride, pH 7.0), fractions collected (each fraction 1 column volume; 6 column) and labelled. If two consecutive fractions were absent in the protein content (UV 280 nm), moved to the next step. Samples were kept on ice during purification. Analysed the protein concentration by UV (280 nm) (Abs of 1 mg/ml of G-CSF was about 0.872). Samples were taken for SDS-PAGE and SE-HPLC. To remove free CA from the mixture, HIC was used. Samples were concentrated, if required.

The AEX fractions containing conjugate were pooled and (NH$_4$)$_2$SO$_4$ added to give a concentration of 2.75M in the loading solution. This solution was then loaded on to the HIC column previously equilibrated with HIC buffer A (10 mM Sodium Phosphate, 2.75M Ammonium Sulphate, pH 6.5). The loading fractions were collected (each fraction 1.5 column volume) and labelled. Washed column with HIC buffer A (at least 5 column volumes; rate=0.5 ml/min; (1.5 column volume) fractions collected and labelled. Eluted the product with HIC buffer B (20 mM sodium phosphate pH 7.4) (rate=5 ml/min); fractions collected (1 column volume fraction; 6 column volume) and labelled. Samples were kept on ice during purification. Protein concentration analyzed by UV (280 nm). The HIC fractions containing the purified conjugate were combined and composition of the conjugate in solution was adjusted with 50% sorbitol solution and 10 mg/ml Tween 20 solution to give a final composition of 5% sorbitol and 0.025 mg/ml Tween 20. The solution was then concentrated at 4±1° C. and protein concentration analysed by UV (280 nm). Further purification can be done by SE-HPLC (e.g. to separate conjugates from free protein/aggregates etc.). Conjugate were sterile filtered and samples taken for activity assay and for characterisation by SDS-PAGE and SE-HPLC. If required an aliquot was removed for protein assay and CA assay. Stored the remainder at 4±1° C. until further use and studied for physical stability by SE-HPLC.

The effects of various processes affecting the stability of GCSF in solution and the degree of derivatization were studied.

Results

The procedure to prepare and purify colominic acid (CA) conjugates (on 20 mg scale) of granulocyte-colony stimulating factor (G-CSF) in an N-terminally selective manner by conducting the reaction at a reduced pH (pH 5.5) and at 4±1° C. is detailed above. This involves conjugation in the presence of sodium cyanoborohydride, followed by purification using ion-exchange chromatography (AEX) to remove free G-CSF followed by removal of CA by hydrophobic interaction chromatography (HIC). The low pH was used to favour selective derivatisation of the alpha amino group of the N-terminus, and also in order to minimise aggregation of GCSF during the reaction. The composition of the final reaction buffer was 5% sorbitol, 0.5 mg/ml Tween 20 in 10 mM NaOAc at pH 5.5.

Formation of the GCSF-CA conjugates was confirmed by the SE-HPLC (change of retention time of GCSF-CS as compared to GCSF; also co-elution of both moieties); ion exchange chromatography (binding of conjugates on to the AEC column) and polyacrylamide gel electrophoresis (SDS-PAGE; shifting of bands with high m.w. species). The conjugates used in the in vitro cell line assay (on MNFS-60 cells) were ~40% active as compared native protein. The conjugates prepared without formulation additives led to the aggregation of protein with poor degree of derivatization. FIG. 3.1, left hand side, shows the SE-HPLC data for GCSF-CA 39 kDa reaction mixture after 24 hours, prepared in the presence of Tween 20. Characterisation conditions were Superdex 200, ammonium bicarbonate 0.15 M pH 7.8. Table 2 shows the peak analysis:

TABLE 2

| Peak | RT | % Area | Species |
| --- | --- | --- | --- |
| 1 | 31.683 | 8.80 | Aggregate |
| 2 | 42.683 | 11.77 | (CA)2-GCSF |
| 3 | 49.058 | 68.55 | CA-GCSF |
| 4 | 68.833 | 10.89 | GCSF |

The right hand side of FIG. 3.1 shows the SDS-PAGE results.

4.1 Preparation of N-Terminal Leptin-CA Conjugates with Formulation Additives

Leptin was supplied as lyophilized powder (m.w. 16.240) and stored at −80° C. The amount of colominic acid (e.g. oxidised or non-oxidised colominic acid; 7.5 molar excess) to be added for conjugation was calculated. Colominic acid was dissolved in minimum quantity of sodium acetate buffer and was filtered and pH was adjusted to 5.5. Colominic acid solution was added in to the Leptin solution (protein in 20 mM sodium acetate, 1% sucrose, 10 mM L-glutamic acid and 0.01% Tween 20 pH5.5) followed by the addition of required µl of NaCNBH$_3$ in order to have 50 mM or 3.17 mg/ml in the reaction mixture, mixed gently and the pH of the final reaction mixture was checked, the pH was adjusted to 5.5. The tube was sealed and was stirred at desired temperature (4±1° C.) for 24 hours. After incubation, necessary sample was taken out (for SDS-PAGE, SE-HPLC etc.). The protein concentration was analysed by UV (280 nm) (Abs of 1 mg/ml of leptin is 0.878). The various process variable affecting the degree of derivatization and stability of the protein were studied.

4.2 Purification and Characterization of Leptin-CA Conjugates

HIC and IEC were used to remove excess CA and free leptin from the reaction mixture respectively. An aliquot was removed for protein assay and CA assay. The reminder was stored at −80° C. until use. Product was characterised by SDS-PAGE, SE-HPLC, western blotting, CA and protein assay etc.

Results

The procedure to prepare and purify colominic acid (CA) conjugates (on 5 mg scale) of Leptin in an N-terminally selective manner by conducting the reaction at a reduced pH (pH 5.5) and at 4±1° C. is shown above. This involves conjugation in the presence of sodium cyanoborohydride, followed by purification using ion-exchange chromatography (AEX) to remove free G-CSF followed by removal of CA by hydrophobic interaction chromatography (HIC). The low pH and formulation additives were used to favour selective derivatisation of the alpha amino group of the N-terminus, and also in order to minimise aggregation of GCSF during the reaction. The composition of the final reaction buffer was (protein in 20 mM sodium acetate, 1% sucrose, 10 mM L-glutamic acid and 0.01% Tween 20 pH5.5).

Formation of the Leptin-CA conjugates was confirmed by the SE-HPLC (change of retention time of Leptin-CA as compared to Leptin; also co-elution of both moieties); ion exchange chromatography (binding of conjugates on to the AEC column) and polyacrylamide gel electrophoresis (SDS-PAGE; shifting of bands with high m.w. species). The conjugates prepared without formulation additives led to the aggregation of protein with poor degree of derivatization.

FIG. 4.1, left hand side, shows SDS-PAGE of 50 kDa CAO-leptin conjugates and the right hand side the SEC-HPLC results.

5.1 Preparation of N-Terminal Erythropoietin (EPO)-CA Conjugates

EPO was supplied as a solution (0.34 mg/ml in 10 mM phosphate buffer 130 mM NaCl pH 7.0; specific activity: 110,000 U/ml, m.w. 30600) and stored at −32° C., protein was defrosted at 2-8° C. and required amount was taken into a 2 ml eppendorf tube. The required amount of colominic acid was taken and the protein solution was added to solid CA and mixed gently. The required µl of sodium cyanoborohydride solution was added to have 50 mM or 3.17 mg/ml in the reaction mixture, vortex and check the pH of the final reaction mixture; if necessary adjust the pH to 7.4. Tube was sealed and stirred at desired temperature (4±1° C.) for 24 hours. After incubation, taken the necessary samples (e.g. for activity assay, SDS-PAGE, SE-HPLC).

5.2 Purification and Characterization of Epo-CA Conjugates

The remaining reaction mixture sample was diluted with HIC buffer A (1.2M Ammonium sulphate, pH 6.3) (1 ml sample+4 ml of buffer A) and loaded on the HIC column previously equilibrated with HIC buffer A. Loading fraction collected and labelled. Column was washed with HIC buffer A (1.2M Ammonium sulphate, pH 6.3) (at least 10 ml) fractions collected and labelled. Eluted the product with HIC buffer B (10 mM Tris buffer pH 7.0), first fraction collected (0.5 ml) and then 0.5-1 ml fractions and labelled. Samples were kept on ice during purification.

Analyse the protein concentration by UV (280 nm) (Abs of 1 mg/ml of EPO was about 0.743). Taken samples for SDS-PAGE. The separation of non-conjugated EPO was performed using anion exchange chromatography (AXC) if CA Mw is too small (e.g. 22 KDa) for separation of conjugate and EPO by SE-HPLC. For AXC the HIC fractions containing protein were diluted with AXC buffer A (10 mM Tris buffer pH 7.0) (1 ml sample+5 ml AXC buffer A) and loaded to the AXC column pre-equilibrated with AXC buffer A. Loading fractions collected and labelled. Column was washed with AXC buffer B (20 mM Sodium Acetate pH 3.0) (at least 10 ml) fractions collected and labelled. Eluted the product with AXC buffer C (50 mM Sodium Phosphate buffer, 1M Sodium Chloride, pH 7.0), first fraction collected (0.5 ml) and then 0.5-1 ml fractions and labelled. Samples were kept on ice during purification.

Alternative purification can be done by SE-HPLC (e.g. to separate conjugates from EPO if CA used has high molecular weight, e.g. 39 kDa). Analysed the protein concentration by UV (280 nm) (Abs of 1 mg/ml of EPO is about 0.743). Taken samples for SDS-PAGE.

An aliquot was removed for protein assay and CA assay. Stored the remainder at −20° C. until use. Products were characterised by SDS-PAGE. To determine the activity of EPO samples in inducing proliferation in vitro of erythrocyte progenitor cells isolated from the spleen of a mouse rendered anaemic artificially through I.P. injection of phenylhydrazine was used. The protocol was adapted based on the method reported by Krystal [1972]. The assay depends on adding EPO to erythrocyte progenitors and measuring the rate of DNA replication by determining the rate of incorporation of $^3$H-thymidine. The in vivo pharmacokinetics (PK) and pharmacodynamics (PD) studies were done in B6D2F1 mice.

Results

Formation of the EPO-CA conjugates was confirmed by the SE-HPLC (change of retention time of EPO-CA as compared to EPO; also co-elution of both moieties); ion exchange chromatography (binding of conjugates on to the AEC column) and polyacrylamide gel electrophoresis (SDS-PAGE; shifting of bands with high m.w. species) (FIG. 5.3). The polysialyted samples were active in vitro and showed vastly superior profile (PK and PD) to plain EPO. FIGS. 5.1 and 5.2 show in vivo results.

FIG. 5.3, left hand side, shows the SE-HPLC of EPO-CA 39 kDa conjugation after 24 hours. Table 3 is the peak analysis table. Characterisation conditions:
column Superdex 200, buffer ammonium bicarbonate 0.15 M, pH 7.8.

TABLE 3

| Peak | RT | % Ar | Species |
|---|---|---|---|
| 1 | 31.421 | 3.38 | Aggregate |
| 2 | 48.346 | 80.76 | CA39-EPO |
| 3 | 59.204 | 15.86 | EPO |

6.1 Preparation of N-Terminal Non-Glycosylated (NGepo-CA) Conjugates

Naked EPO was supplied as a solution (0.18 mg/ml in 20 mM sodium phosphate buffer 300 mM NaCl pH 6.65; specific activity 100000 U/ml; m.w. 19000) and stored at −32° C., protein defrosted at 2-8° C. and taken the required amount into a 2 ml eppendorf. Calculated the amount of colominic acid (e.g. oxidised or non-oxidised colominic acid) to be added for conjugation. Weighed out the required amount of colominic acid and recorded the weight. Protein solution was added to solid CA and mixed gently. Added the required μl solution of sodium cyanoborohydride in order to have 50 mM or 3.17 mg/ml in the reaction mixture, vortexed and pH checked of the final reaction mixture; if necessary adjusted the pH to 7.4. Tube was sealed and stirred at desired temperature (4±1° C.) for 24 hours. After incubation, taken the necessary samples (e.g. for activity assay, SDS-PAGE, SE-HPLC).

6.2 Purification and Characterization of NGepo-CA Conjugates

The remaining reaction mixture sample was diluted with HIC buffer A (1.2M Ammonium sulphate, pH 6.3) (1 ml sample+4 ml of buffer A) and loaded on the HIC column previously equilibrated with HIC buffer A. Loading fractions collected and labelled. Column was washed with HIC buffer A (at least 10 ml) fractions collected and labelled. Eluted the product with HIC buffer B, first fraction collected (0.5 ml) and then 0.5-1 ml fractions and labelled. Samples were kept on ice during purification. Analysed the protein concentration by UV (280 nm) (Abs of 1 mg/ml of nEPO was about 0.743). Taken samples for SDS-PAGE. The reaction conditions led to no free naked EPO in the reaction mixture so no further purification was necessary. If naked EPO was present in the reaction mixture, the HIC fractions containing protein was concentrated using Vivaspin 6 (5000 MWCO) & purification can be done by SE-HPLC. Analysed the protein concentration by UV (280 nm) (Abs of 1 mg/ml of nEPO is about 0.743). Taken samples for SDS-PAGE.

An aliquot was removed for protein assay and CA assay. Stored the remainder at −20° C. until use. Product can be characterised by SDS-PAGE.

Results

Formation of the NGepo-CA conjugates was confirmed by the SE-HPLC (change of retention time of NGepo-CA as compared to NGEPO; also co-elution of both moieties); ion exchange chromatography (binding of conjugates on to the AEC column) and polyacrylamide gel electrophoresis (SDS-PAGE; shifting of bands with high m.w. species). (FIGS. 6.1 to 6.3). FIG. 6.3, left hand side, shows EPO-CA 39 kDa conjugation after 24 hours. The polysialyted samples were active in vitro and showed vastly superior profile (PK and PD) to plain NGepo.

FIG. 6.3 shows the SE-HPLC results. The peak analysis is shown in table 4 below. Characterisation conditions—column Superdex 200, buffer ammonium bicarbonate 0.15 M, pH 7.8.

TABLE 4

| Peak | RT | % Ar | Species |
|---|---|---|---|
| 1 | 31.863 | 3.41 | Aggregate |
| 2 | 33.212 | 6.65 | Aggregate |
| 3 | 42.667 | 14.72 | (CA)2-nEPO |
| 4 | 48.571 | 74.49 | CA-nEPO |
| 5 | 68.183 | 0.73 | nEPO |

FIG. 6.1 shows the in vivo clearance results. PSA-NGEPO showed a vastly superior profile as compared to NGEPO.

7.1 Preparation of N-Terminal Insulin-CA Conjugates

The insulin was dissolved by minimum 100 mM HCl and then adjusted to the required pH. Amount of colominic acid (e.g. oxidised or non-oxidised colominic acid) was calculated for conjugation. Required amount of colominic acid was weighed out and dissolved in the minimum volume of reaction buffer, added to the protein solution and gently mixed using a vortex mixer. Required μl of sodium cyanoborohydride was added to give final concentration of 4 mg per ml of reaction mixture. Suitable stabilizer was used if required in the reaction mixture. Tube was sealed and stirred at desired temperature (37° C.; as appropriate) for 48 hours. The time and temperature may vary according to the protein used. Polysialylated protein purified by an IEC and HIC. 100% protein-polymer conjugation was achieved after 24 hours. It was characterised by native-page, SDS-page, size-exclusion chromatography, ion-exchange chromatography etc.

In IEC, to purify insulin and insulin-colominic acid conjugates by cation exchange chromatography over a High Trap SP column in order to separate polysialylated insulin (does not bind to column) from free insulin (which is retained on the column). This involves separation of conjugate below its isoelectric point of 5.2 (at least one unit below) using cation-exchange resin. The activity of these conjugates were determined on healthy mice.

7.2 Purification and Characterization of Insulin-CA Conjugates

The reaction mixture sample was diluted 5 times with AEX buffer A (0.05M sodium acetate pH 4.4), pH was checked and adjusted if required to pH 4.4, loaded on the AEX column (rate=1 ml/min) previously equilibrated with AEX buffer A. The loading fractions were collected (each fraction 1.5 column volume) and labelled. Washed column with AEX buffer A (0.05M Sodium acetate pH 4.4) (at least 5 column volume, rate=1 ml/min), fractions collected (each fraction 1.5 column volume) and labelled. Eluted the product with AEX buffer B (0.05M sodium acetate, 1M sodium chloride, pH 4.4) (rate=1 ml/min), fractions collected (each fraction 1 column volume; 6 column) and labelled. If two consecutive fractions were absent in the protein content, moved to the next step. Samples were kept on ice during purification.

The AEX fractions containing conjugate were pooled and diluted 10 times with HIC buffer A (0.8 M Ammonium sulphate, 50 mM sodium phosphate, pH 7.4), pH adjusted to 7.4 with hydrochloric acid solution or sodium hydroxide solution. This solution was then loaded on to the HIC column (rate=0.3 ml/min) previously equilibrated with HIC buffer A (0.8 M Ammonium sulphate, 50 mM sodium phosphate, pH 7.4). The loading fractions were collected (each fraction 1.5 column volume) and labelled. Washed column with HIC buffer A (at least 5 column volumes; rate=0.5 ml/min; (1.5 column volume) fractions collected and labelled. Eluted the product with HIC buffer B (50 mM sodium phosphate pH 7.4) (rate=5 ml/min); fractions collected (1 column volume fraction; 6 column volume) and labelled. Samples were kept on ice during purification. Protein concentration analyzed by UV (280 nm). The HIC fractions containing the purified conjugate were combined & concentrated at 4±1° C. and protein concentration analysed by UV (280 nm).

Results

Formation of the insulin-CA conjugates was confirmed by the SE-HPLC (change of retention time of insulin-CA as compared to insulin; also co-elution of both moieties); ion exchange chromatography (elution of conjugates on to the CEC column) and polyacrylamide gel electrophoresis (SDS-PAGE; shifting of bands with high m.w. species). (FIGS. 7.1 to 7.2). The polysialyated samples showed superior in vivo efficacy as compared to native protein.

In FIG. 7.2 the HPLC conditions are as follows: Column: Superose 12; Buffer: Sodium phosphate 0.1M (pH 6.9); Flow rate: 0.25 ml/min; Injection volume: 200 µl.

8.1 Preparation of N-Terminal Interferon-CA Conjugates

The procedure to prepare and purify colominic acid (CA) conjugates of IFNalpha2b involves conjugation in the presence of sodium cyanoborohydride, followed by purification by HIC to remove free colominic acid followed by removal of non-conjugated IFN by either AXC or SE-HPLC (if any) (example 1 mg scale). IFNalpha2b was supplied as a solution (1.75 mg/ml in acetate buffer pH 5) and stored at −32° C. Protein was defrosted at 2- and taken the required amount into a 2 ml eppendorf tube. If the protein concentration in the reaction mixture was lower than 1.75 mg/ml then it was diluted with the required amount of PBS pH 7.4.

Required amount of CA was weighed out & recorded. CA was solubilised in the minimum volume of reaction buffer, added to the protein solution and gently mixed using a vortex. Added the required µl in order to have 50 mM or 3.17 mg/ml in the reaction mixture, gently mixed and pH of the final reaction mixture was checked; if necessary adjusted the pH to 6.0. Tube was sealed and stirred at desired temperature (4±1° C.) for 24 hours. Necessary samples were taken after incubation time (e.g. for activity assay, SDS-PAGE, SE-HPLC).

8.2 Purification and Characterization of Interferon-CA Conjugates

The remaining reaction mixture sample was diluted with HIC buffer A (25 mM Tris buffer, 3M sodium chloride, pH 7.5) (1 ml sample+4 ml of buffer A) and loaded on the HIC column previously equilibrated with HIC buffer A. Loading fractions collected and labelled. Column was washed with HIC buffer A (25 mM Tris buffer, 3M sodium chloride, pH 7.5) (at least 10 ml) fractions collected and labelled. Column was eluted with HIC buffer B (25 mM Tris buffer pH 7.5), first fraction (0.5 ml) collected and then 0.5-1 ml fractions were collected and labelled. Samples were kept on ice during purification.

Protein concentration analyzed by UV (280 nm) (Abs of 1 mg/ml of IFN is about 1). Samples for SDS-PAGE were taken.

The separation of non-conjugated IFN was performed using anion exchange chromatography (AXC) or SE-HPLC. For AXC, the HIC fractions containing protein were diluted with AXC buffer A (25 mM Tris buffer pH 7.5) (1 ml sample+5 ml AXC buffer A) and loaded to the AXC column pre-equilibrated with AXC buffer A. Loading fractions collected and labelled. Column was washed with AXC buffer B (50 mM Sodium Phosphate, 150 mM sodium chloride, pH 5) (at least 10 ml), fractions collected and labelled. Product was eluted with AXC buffer C (50 mM Sodium Phosphate, 1M sodium chloride, pH 7), first fraction collected (0.5 ml) and then 0.5-1 ml fractions and labelled. Samples were kept on ice during purification.

Further purification done by SE-HPLC (e.g. to separate di-conjugates from mono-conjugates). (FIG. 8.1)

Protein concentration was analyzed by UV (280 nm) (Abs of 1 mg/ml of IFN is about 1) or by BCA assay. Samples were taken for SDS-PAGE. An aliquot was removed for protein assay and CA assay. The remaining product was stored at −20° C. until use. Product was characterised by SDS-PAGE. The activity was determined on daudi cell line.

Results

Formation of the interferon-CA conjugates was confirmed by the SE-HPLC (change of retention time of interferon-CA as compared to interferon; also co elution of both moieties); ion exchange chromatography (binding of conjugates on to the AEC column) and polyacrylamide gel electrophoresis (SDS-PAGE; shifting of bands with high m.w. species).

(FIGS. 8.1 to 8.2). The polysialyted samples were active in vitro and showed vastly superior profile (PK) to plain Interferon.

Table 5 shows the peak analysis of the SE-HPLC in FIG. 8.1.

TABLE 5

| Aggregate | Rt | % Area |
|---|---|---|
|  | 32.1 | 4.3 |
| CA-IFN (di-) | 55.1 | 9.7 |
| CA-IFN (mono-) | 62.4 | 56.2 |
| Free IFN | 74.7 | 29.4 |

9.1. Polysialylation of Obestatin

Obestatin is a 2.5 kDa appetite suppressing hormone. Whilst encoded by the ghrelin gene, obestatin opposes ghrelins appetite-stimulating effects. Obestatin treatment of rats has been shown to suppress food intake, inhibit jejunal contraction, and decrease weight gain.

9.2 N-Terminal Conjugation (Site-Specific)

15 molar excess of oxidised 14 kDa polysialic acid (PSA) was dissolved in buffer and the pH adjusted to 6.0. Obestatin and 50 mM (final concentration) sodium cyanoborohydride was then added, the pH re-adjusted, and reaction mixture brought to the required volume. Reactions were carried out at 4±1° C. with gentle shaking for 18 hours.

9.3 Random Conjugation (Comparative)

10 molar excess of oxidised 14 kDa PSA was dissolved in buffer and the pH adjusted to 7.4. Obestatin and 50 mM (final concentration) sodium cyanoborohydride was then added, the pH re-adjusted, and reaction mixture brought to the required volume. Reactions were carried out at 4±1° C. with gentle shaking for 18 hours.

Analysis of Conjugation

Conjugation is confirmed by decrease in retention time, thus increased size, on size-exclusion-high performance liquid chromatography (SE-HPLC). 100 µL of conjugation reaction was injected onto SE-HPLC Superose 12 column pre-equilibrated in 0.1M sodium phosphate pH 6.9, with a flow rate of 0.25 mL/min. Absorbance at 280 nm was recorded.

Conjugates are visualised by decrease in mobility on a sodium dodecyl sulfate polyacrylamide gel electrophoresis (SDS-PAGE) gel (FIG. 9). Samples were electrophoresed on a 4-20% tris-glycine gel under non-denaturing conditions. Lane 1: Molecular weight markers; 2: Obestatin; 3: pH 6.0 reaction; 4: pH 7.4 reaction.

As confirmed by SE-HPLC obestatin-PSA conjugates were successfully created at both pH 6.0 and pH 7.4. Conjugates created at pH 7.4 are also visualized by SDS-PAGE.

10.1 Polysialylation of DNaseI

In cystic fibrosis (CF) patients, retention of viscous purulent secretions in the airways contributes to both reduced pulmonary function and to exacerbation of infections. Purulent pulmonary secretions contain very high concentrations of extracellular DNA which is released by degenerating leukocytes that accumulate in response to infection. Treatment of CF patients with Deoxyribonuclease I (DNase I) hydrolyzes the DNA, thus reducing sputum viscoelasticity. It has also been proposed for the treatment of systemic lupus erythematosus and tumour targeting.

10.2 N-Terminal Conjugation (Site Specific)

20 molar excess of oxidised 26 kDa polysialic acid (PSA) was dissolved in buffer and the pH adjusted to 6.0. Bovine DNaseI (Samsong & Sigma) and 50 mM (final concentration) sodium cyanoborohydride was then added, the pH re-adjusted, and reaction mixture brought to the required volume. Reactions were carried out at 37±1° C. and 4±1° C. with gentle shaking for 18 hours.

10.3 Random Conjugation (Comparative)

10-50 molar excess of oxidised 14 kDa PSA was dissolved in buffer and the pH adjusted to 7.4. Bovine DNaseI (Samsong & Sigma) and 50 mM (final concentration) sodium cyanoborohydride was then added, the pH re-adjusted, and reaction mixture brought to the required volume. Reactions were carried out at 37±1° C. and 4±1° C. with gentle shaking for 18 hours.

10.4 Analysis of Conjugation

Conjugates were visualised by decrease in mobility on a sodium dodecyl sulfate polyacrylamide gel electrophoresis (SDS-PAGE) gel (FIG. 10.1). Samples were electrophoresed on a 4-20% tris-glycine gel under non-denaturing conditions.

Lane 1: Molecular weight markers; 2: Blank; 3: DNaseI; 4: Sigma DNaseI; 5: Blank; 6: DNaseI with unoxidised PSA; 7: DNaseI oxidised PSA pH 7.4 reaction; 8: DNaseI oxidised PSA pH 6.0 reaction 10.5 Purification of Conjugates DNaseI-PSA conjugates were purified using hydrophobic interaction chromatography (HIC)—Phenyl-sepharose matrix, starting buffer containing 2.0 M ammonium sulphate, elution in buffer without ammonium sulphate. Elution fractions are then applied to ion exchange matrix Q-sepharose Fast Flow, and eluted with buffer containing sodium chloride. Purification of conjugates was confirmed by size-exclusion-high performance liquid chromatography (SE-HPLC) (FIG. 10.2). 100 µL of conjugation reaction was injected onto SE-HPLC Superose 12 column pre-equilibrated in 0.1 M sodium phosphate pH 6.9, with a flow rate of 0.25 mL/min. Absorbance at 280 nm was recorded.

DNaseI-PSA conjugates show decreased retention time in a size exclusion column compared to DNaseI alone.

10.6 Purification of Active DNaseI

Active DNaseI was purified from a mix of active and heat-inactivated DNaseI by heparin-sepahrose chromatography. DNaseI mixture was applied to the column in low salt buffer, and eluted with an increasing gradient of sodium chloride. The activity per mg of DNaseI in fraction A12 was approximately 4 fold higher than that of the sample.

10.7 Activity of Conjugates

Activity conjugates were measured and compared to that of unconjugated DNaseI using the methyl-green assay (Sinicropi et. al., (1994) Anal Biochem, 222(2):351-8). Purified DNaseI-PSA conjugates created at 37±1° C. showed approximately 10% activity (in 4 mM $CaCl_2$ buffer (see below)) compared with non-conjugated DNaseI.

The effect of $CaCl_2$ titration on the DNA hydrolysis activity of DNaseI and the DNaseI-PSA conjugates was measured (n=1) (FIG. 10.3). $CaCl_2$ is a formulation additive. Methyl-green DNaseI assay was set up and additional $CaCl_2$ added. The activity is expressed relative to the activity in 4 mM $CaCl_2$ buffer. DNaseI methyl-green assay was set up with conjugated and free-DNaseI, and $CaCl_2$ added at varying concentrations to a maximum concentration of 100 mM. It was found that addition of $CaCl_2$ increased the activity of conjugated DNaseI more than that of the free-DNaseI. Thus more $CaCl_2$ is required for full activity of DNaseI-PSA conjugates.

CONCLUSION

Active DNaseI-PSA conjugates have been created in the presence of sodium cyanoborohydride. The conjugates have been purified from free-DNaseI and show approximately 10% activity per mg of DNaseI, compared to that of free-DNase.

REFERENCES

Fernandes, A. I., Gregoriadis, G., Polysialylated asparaginase: preparation, activity and pharmacokinetics, Biochimica et Biophysica Acta, 1341 (1997) 26-34.
Fernandes, A. I., Gregoriadis, G., Synthesis, characterization and properties of polysialylated catalase, Biochimica et Biophysica Acta, 1293 (1996) 92-96.
Gregoriadis, G., McCormack, B., Wang, Z., Lifely, R., Polysialic acids: potential in drug delivery, FEBS Letters, 315 (1993) 271-276.
Jain, S., Hirst, D. H., McCormack, B., Mital, M., Epenetos, A., Laing, P., Gregoriadis, G., Polysialylated insulin: synthesis, characterization and biological activity in vivo, Biochemica et. Biophysica Acta, 1622 (2003) 42-49.
Jain, S., Hirst, D. H., Laing, P., Gregoriadis, G., Polysialylation: The natural way to improve the stability and pharmacokinetics of protein and peptide drugs, Drug Delivery Systems and Sciences, 4(2) (2004) 3-9.
Kinstler, O, Molineux, G., Treuheit, M., Ladd, D. and Gegg, C., Mono-N-terminal poly(ethylene glycol)-protein conjugates, Advanced drug delivery reviews, 54 (4), 2002, 477-485.
Lifely, R., Gilhert, A. S., Moreno, C. C., Sialic acid polysaccharide antigen of *Neisseria meningitidis* and *Escherichia coli*: esterification between adjacent residues, Carbohydrate Research, 94 (1981) 193-203.
Park, J. T., Johnson, M. J., A submicrodetermination of glucose, Journal of Biological Chemistry, 181 (1949) 149-151.
Shriner, R. L., Fuson, R. D. C., Curtin, D. Y., Morill, T. C., The Systematic Identification of Organic Compounds, 6th ed., Wiley, New York, 1980.
Svennerholm, L., Quantitative estimation of sialic acid II: A colorimetric resorcinol-hydrochloric acid method, Biochimca et Biophysica Acta, 24 (1957) 604-611.
Wang, W. Instability, stabilization, and formulation of liquidprotein pharmaceticals, International Journal of Pharmaceutics, 185 (1999) 129-188.
Krystal, Exp Hematol 1983, 11(7), 649-660.

The invention claimed is:

1. A composition comprising a population of polysialic acid derivatives of a DNase protein, wherein the derivatives comprise between 2 and 200 sialic acid units and wherein at least 85% of the population is derivatised with polysialic acid at the N-Terminal amine only.
2. The composition of claim 1, wherein at least 90% of the population is derivatised with polysialic acid at the N-Terminal amine only.
3. The composition of claim 1, wherein the DNase is DNase I.
4. The composition of claim 1, wherein the derivatives comprise 2-120 sialic acid units.
5. The composition of claim 1, further comprising one or more pharmaceutically acceptable excipients.
6. The composition of claim 1, wherein the polysialic acid is linked to the protein via a linker.
7. The composition of claim 1, wherein the derivatives has a polydispersity of less than 1.3.
8. A polysialic derivative according to formula (I)

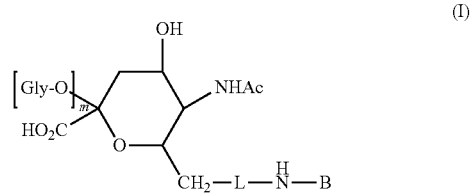

wherein m is 2-200;
HNB is derived from B—NH2 which is the N-terminal amine of a DNase protein, L is

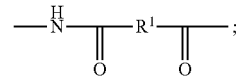

GlyO is a sialic acid unit; and
wherein $R^1$ is selected from the group consisting of alkanediyl, arylene, alkarylene, heteroarylene and alkylheteroarylene, any of which may be substituted and/or interrupted by carbonyl, ester, sulfide, ether, amide and/or amine linkages.
9. The composition of claim 8, wherein the DNase is DNase I.
10. The composition according to claim 8, wherein the derivatives comprise 2-120 sialic acid units.
11. The composition according to claim 8, further comprising one or more pharmaceutically acceptable excipients.
12. A method for producing the purified N-terminal derivative of a DNase protein of claim 8, comprising reacting (i) a Polysialic acid (PSA) with DNase at the amine group of the N-terminus of the DNase in aqueous acidic solution to produce an N-terminal derivative; and (ii) purifying the resultant N-terminal derivative in an aqueous solution of higher pH than in step (i) to obtain a population of derivatives comprising between 2 and 200 sialic acid units and wherein at least 85% of the population is derivatised with polysialic acid at the N-Terminal amine only.
13. The method of claim 12, wherein the DNase is DNase I.
14. The method according to claim 12, wherein the PSA comprises at least one sialic acid unit or moiety derived from a sialic acid unit.
15. The method according to claim 12, wherein the PSA comprises a sialic acid unit or moiety derived from a sialic acid unit at its non-reducing and/or reducing end.
16. The method according to claim 12, wherein the PSA consists substantially only of units of sialic acid.
17. The method according to claim 12, wherein the pH of the aqueous solution in step (i) is in the range 4.0-6.0 and in step (ii) is in the range 6.5-8.5.
18. An N-terminal derivative of DNase which is obtainable by a method according to claim 12.
19. A method for treating cystic fibrosis, lupus, or a tumor comprising administering the composition of claim 1 to a patient in need thereof.

* * * * *